US006001809A

United States Patent [19]
Thorsett et al.

[11] Patent Number: 6,001,809
[45] Date of Patent: Dec. 14, 1999

[54] INHIBITORS OF LEUKOCYTE ADHESION

[75] Inventors: Eugene D. Thorsett, Moss Beach; Theodore A. Yednock, Fairfax; Michael A. Pleiss, Fremont, all of Calif.

[73] Assignee: Elan Pharmaceuticals, Inc., South San Francisco, Calif.

[21] Appl. No.: 08/467,580

[22] Filed: Jun. 6, 1995

Related U.S. Application Data

[63] Continuation-in-part of application No. 08/273,055, Jul. 11, 1994, abandoned.

[51] Int. Cl.$^6$ .................................................. A61K 38/00
[52] U.S. Cl. ................................ 514/15; 514/16; 514/17; 514/18; 514/903; 530/327; 530/328; 530/329; 530/330
[58] Field of Search ................................ 514/15, 16, 17, 514/18, 903; 530/327, 328, 329, 330

[56] References Cited

U.S. PATENT DOCUMENTS

| | | | |
|---|---|---|---|
| 4,235,871 | 11/1980 | Papahadjopoulos et al. | 424/19 |
| 4,501,728 | 2/1985 | Geho et al. | 424/38 |
| 4,542,124 | 9/1985 | Huffman et al. | 514/11 |
| 4,837,028 | 6/1989 | Allen | 424/450 |
| 5,066,716 | 11/1991 | Robey et al. | 525/54.1 |
| 5,473,051 | 12/1995 | Altieri et al. | 530/382 |
| 5,510,332 | 4/1996 | Kogan et al. | 514/14 |

FOREIGN PATENT DOCUMENTS

| | | |
|---|---|---|
| 330506 | 8/1989 | European Pat. Off. . |
| WO 88/07055 | 9/1988 | WIPO . |
| WO 91/05038 | 4/1991 | WIPO . |
| 91/18011 | 11/1991 | WIPO . |
| 92/01464 | 2/1992 | WIPO . |
| 94/05310 | 3/1994 | WIPO . |
| 94/25482 | 11/1994 | WIPO . |

OTHER PUBLICATIONS

Elices, et al., *Cell*, 60:577–584 (1990).
Springer, *Nature*, 346:425–434 (1990).
Osborn, *Cell*, 62:3–6 (1990).
Vedder, et al., *Surgery*, 106:509–516 (1989).
Pretolani, et al., *J. Exp. Med.*, 180:795–805 (1994).
Abraham, et al., *J. Clin. Invest.*, 93:776–787 (1994).
Mulligan, et al., *J. Immunology*, 150(6):2407–2417 (1993).
Cybulsky, et al., *Science*, 251:788–790 (1991).
Li, et al., *Arteriosclcer. Thromb.*, 13(2):197–204 (1993).
Sasseville, et al., *Am. J. Path.*, 144(1):27–40 (1994).
Yang, et al., *Proc. Nat. Acad. Science (USA)*, 90:10494–10498 (1993).
Burkly, et al., *Diabetes*, 43:529–534 (1994).
Baron, et al., *J. Clin. Invest.*, 93:1700–1708 (1994).
Hamann, et al., *J. Immunology*, 152:3282–3293 (1994).
Yednock, et al., *Nature*, 356:63–66 (1992).
Baron, et al., *J. Exp. Med.*, 177:57–68 (1993).
van Dinther–Janssen, et al., *J. Immunology*, 147(12):4207–4210 (1991).
van Dinther–Janssen, et al., *Annals. Rheumatic Dis.*, 52:672–676 (1993).
Elices, et al., *J. Clin. Invest.*, 93:405–416 (1994).
Postigo, et al., *J. Clin. Invest.*, 89:1445–1452 (1992).
Paul, et al., *Transpl. Proceed.*, 25(1):813–814 (1993).
Okarhara, et al., *Can. Res.*, 54:3233–3236 (1994).
Paavonen, et al., *Int. J. Can.*, 58:298–302 (1994).
Schadendorf, et al., *J. Path.*, 170:429–434 (1993).
Bao, et al., *Diff.*, 52:239–246 (1993).
Lauri, et al., *British J. Cancer*, 68:862–867 (1993).
Kawaguchi, et al., *Japanese J. Cancer Res.*, 83:1304–1316 (1992).
Matteucci, et al., *J. Am. Chem. Soc.* 103:3185–3191 (1981).
Robey, et al., *Anal. Biochem.*, 177:373–377 (1989).
Verhoef, et al., *Eur. J. Drug Metab. Pharmacokin.*, 11(4):291–302 (1986).
Langer, *Science*, 249:1527–1535 (1990).
Szoka et al., *Ann. Rev. Biophys. Bioeng.*, 9:467–508 (1980).
Wayner and Kovach, *J. Cell Biol.*, 116(2):489–497 (1992).
Vonderheide, et al., *J. Cell Biol.*, 125(1):215–222 (1994).
van de Weil–van Kemenade, et al., *J. Cell Biol.*, 117(2):461–470 (1992).
Arroyo, et al., *J. Cell Biol.*, 117(3):659–670 (1992).
Vilhardt et al., *Journal of Pharmacology*, 232, pp. 223–226, 1993.
Smith et al., *Cancer Research*, vol. 45, pp. 6119–6123, 1985.
Kopple, Kenneth, *Peptides and Amino Acids*, pp. 32–51, 1966.
Caplus AN: 1986:32815, Smith et al., *Cancer Research.*, 45 (12, pt. 1), 6119–23, 1985.

*Primary Examiner*—Cecilia J. Tsang
*Assistant Examiner*—C. Delacroix-Muirheid
*Attorney, Agent, or Firm*—Carol A. Stratford; Jean M. Duvall; Burns, Doane, Swecker & Mathis, LLP

[57] ABSTRACT

This invention provides peptides which block cellular adhesion mediated by VLA-4. The peptides can be used to treat a number of inflammatory diseases, in particular, inflammatory brain disorders.

13 Claims, 1 Drawing Sheet

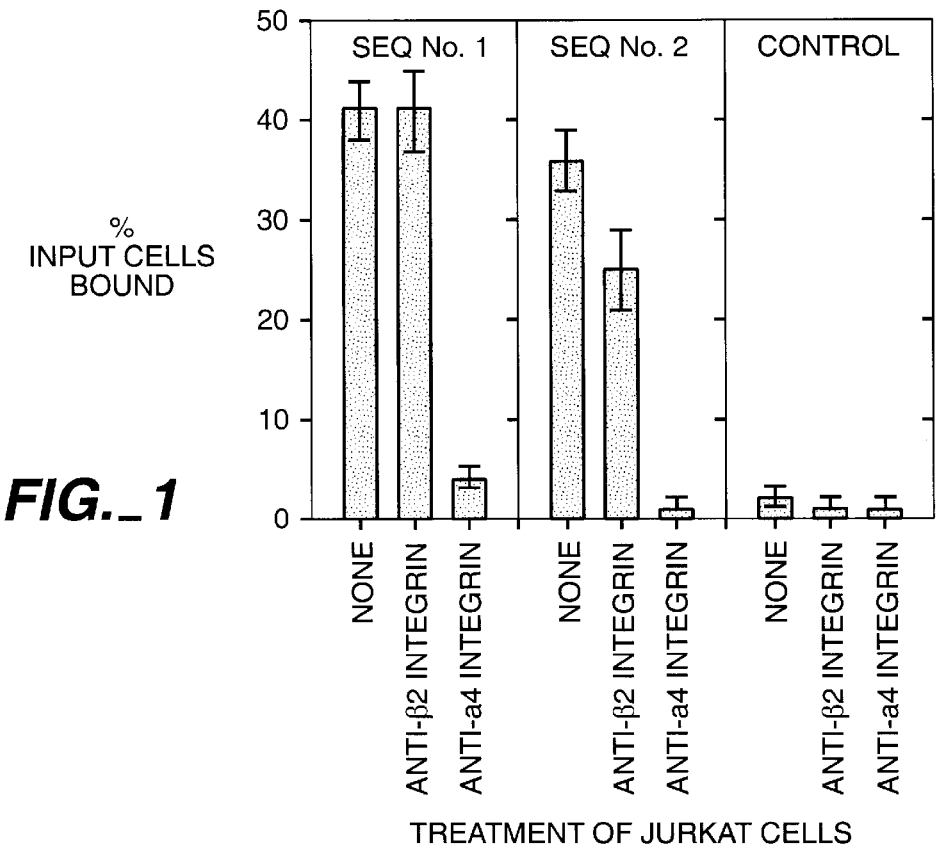
FIG._1
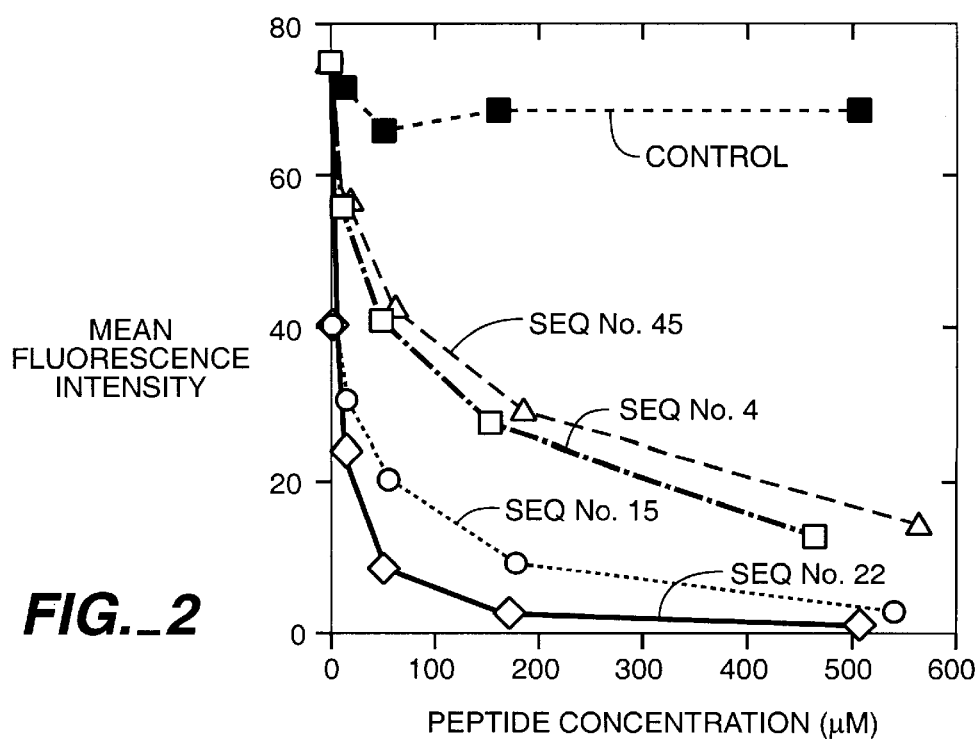
FIG._2

SEQUENCE LISTING

```
<160> NUMBER OF SEQ ID NOS: 163

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Peptide
      fragment derived from 21/6 CDR3 region of
      anti-alpha-4 integrin antibody
<220> FEATURE:
<221> NAME/KEY: MOD_RES
<222> LOCATION: (1)
<223> OTHER INFORMATION: ACETYLATION

<400> SEQUENCE: 1

Cys Gly Gly Glu Gly Tyr Tyr Gly Asn Tyr Gly Val Tyr Ala
  1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Peptide
      derived from fibronectin
<220> FEATURE:
<221> NAME/KEY: MOD_RES
<222> LOCATION: (1)
```

```
<223> OTHER INFORMATION: ACETYLATION

<400> SEQUENCE: 2

Cys Gly Gly Glu Ile Leu Asp Val Pro Ser Thr
 1               5                  10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Peptide
      derived from fibronectin
<220> FEATURE:
<221> NAME/KEY: MOD_RES
<222> LOCATION: (1)
<223> OTHER INFORMATION: ACETYLATION

<400> SEQUENCE: 3

Glu Ile Leu Asp Val Pro Ser Thr
 1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Peptide
      derived from CDR3 region of anti-alpha-4 integrin
      antibody 21/6
<220> FEATURE:
<221> NAME/KEY: MOD_RES
<222> LOCATION: (1)
<223> OTHER INFORMATION: ACETYLATION

<400> SEQUENCE: 4

Glu Gly Tyr Tyr Gly Asn Tyr Gly Val Tyr Ala
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Peptide
      derived from CDR3 region of anti-alpha-4 integrin
      antibody 21/6

<400> SEQUENCE: 5

Glu Gly Tyr Tyr Gly Asn Tyr Gly Val Tyr Ala
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Alanine
      substituted peptide derived from antibody 21/6
<220> FEATURE:
<221> NAME/KEY: MOD_RES
<222> LOCATION: (1)
<223> OTHER INFORMATION: ACETYLATION

<400> SEQUENCE: 6

Ala Gly Tyr Tyr Gly Asn Tyr Gly Val Tyr Ala
 1               5                  10

<210> SEQ ID NO 7
<211> LENGTH: 11
```

-continued

```
<212> TYPE: PRT
<213> ORGANISM: Artificial Sequence
<220> FEATURE:
<223> OTHER INFORMATION: Description of Artificial Sequence:
      Alanine-substituted peptide derived from antibody
      21/6
<220> FEATURE:
<221> NAME/KEY: MOD_RES
<222> LOCATION: (1)
<223> OTHER INFORMATION: ACETYLATION

<400> SEQUENCE: 7

Glu Gly Ala Tyr Gly Asn Tyr Gly Val Tyr Ala
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence:
      Alanine-substituted peptide derived from antibody
      21/6
<220> FEATURE:
<221> NAME/KEY: MOD_RES
<222> LOCATION: (1)
<223> OTHER INFORMATION: ACETYLATION

<400> SEQUENCE: 8

Glu Gly Tyr Ala Gly Asn Tyr Gly Val Tyr Ala
 1               5                  10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Alanine
      substituted peptide derived from antibody 21/6
<220> FEATURE:
<221> NAME/KEY: MOD_RES
<222> LOCATION: (1)
<223> OTHER INFORMATION: ACETYLATION

<400> SEQUENCE: 9

Glu Gly Tyr Tyr Gly Ala Tyr Gly Val Tyr Ala
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence:
      Glutamine-substituted peptide derived from
      antibody 21/6
<220> FEATURE:
<221> NAME/KEY: MOD_RES
<222> LOCATION: (1)
<223> OTHER INFORMATION: ACETYLATION

<400> SEQUENCE: 10

Glu Gly Tyr Tyr Gly Gln Tyr Gly Val Tyr Ala
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence:
      Alanine-substituted peptide derived from antibody
```

```
              21/6
<220> FEATURE:
<221> NAME/KEY: MOD_RES
<222> LOCATION: (1)
<223> OTHER INFORMATION: ACETYLATION

<400> SEQUENCE: 11

Glu Gly Tyr Tyr Gly Asn Ala Gly Val Tyr Ala
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence:
      Alanine-substituted peptide derived from antibody
      21/6
<220> FEATURE:
<221> NAME/KEY: MOD_RES
<222> LOCATION: (1)
<223> OTHER INFORMATION: ACETYLATION

<400> SEQUENCE: 12

Glu Gly Tyr Tyr Gly Asn Tyr Gly Val Ala Ala
 1               5                  10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence:
      Alanine-substituted peptide derived from antibody
      21/6
<220> FEATURE:
<221> NAME/KEY: MOD_RES
<222> LOCATION: (1)
<223> OTHER INFORMATION: ACETYLATION

<400> SEQUENCE: 13

Glu Gly Ala Tyr Gly Asn Ala Gly Val Tyr Ala
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence:
      Alanine-substituted peptide derived from antibody
      21/6
<220> FEATURE:
<221> NAME/KEY: MOD_RES
<222> LOCATION: (1)
<223> OTHER INFORMATION: ACETYLATION

<400> SEQUENCE: 14

Glu Gly Ala Tyr Gly Asn Tyr Gly Val Ala Ala
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence:
      Alanine-substituted peptide derived from antibody
      21/6
<220> FEATURE:
<221> NAME/KEY: MOD_RES
<222> LOCATION: (1)
```

<223> OTHER INFORMATION: ACETYLATION

<400> SEQUENCE: 15

Glu Gly Tyr Tyr Gly Asn Ala Gly Val Ala Ala
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence :
      Alanine-substituted peptide derived from antibody
      21/6
<220> FEATURE:
<221> NAME/KEY: MOD_RES
<222> LOCATION: (1)
<223> OTHER INFORMATION: ACETYLATION

<400> SEQUENCE: 16

Glu Gly Ala Tyr Gly Asn Ala Gly Val Ala Ala
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence:
      Alanine-substituted peptide derived from antibody
      21/6

<400> SEQUENCE: 17

Glu Gly Tyr Tyr Gly Asn Tyr Gly Val Tyr
 1               5                  10

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Peptide
      derived from antibody 21/6

<400> SEQUENCE: 18

Glu Gly Tyr Tyr Gly Asn Tyr Gly Val
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Peptide
      derived from antibody 21/6

<400> SEQUENCE: 19

Glu Gly Tyr Tyr Gly Asn Tyr Gly
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Peptide
      derived from antibody 21/6

<400> SEQUENCE: 20

```
Glu Gly Tyr Tyr Gly Asn Tyr
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Peptide
      derived from antibody 21/6

<400> SEQUENCE: 21

Glu Gly Tyr Tyr Gly Asn
  1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence:  Peptide
      derived from antibody 21/6

<400> SEQUENCE: 22

Glu Gly Tyr Tyr Gly Asn Tyr Gly Val Tyr
  1               5                  10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Peptide
      derived from antibody 21/6
<220> FEATURE:
<221> NAME/KEY: MOD_RES
<222> LOCATION: (1)
<223> OTHER INFORMATION: ACETYLATION

<400> SEQUENCE: 23

Glu Gly Tyr Tyr Gly Asn Tyr Gly Val
  1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:  Peptide
      derived from antibody 21/6
<220> FEATURE:
<221> NAME/KEY: MOD_RES
<222> LOCATION: (1)
<223> OTHER INFORMATION: ACETYLATION

<400> SEQUENCE: 24

Glu Gly Tyr Tyr Gly Asn Tyr Gly
  1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:  Peptide
      derived from antibody 21/6
<220> FEATURE:
<221> NAME/KEY: MOD_RES
<222> LOCATION: (1)
<223> OTHER INFORMATION: ACETYLATION
```

```
<400> SEQUENCE: 25

Glu Gly Tyr Tyr Gly Asn Tyr
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Peptide
      derived from antibody 21/6
<220> FEATURE:
<221> NAME/KEY: MOD_RES
<222> LOCATION: (1)
<223> OTHER INFORMATION: ACETYLATION

<400> SEQUENCE: 26

Glu Gly Tyr Tyr Gly Asn
 1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Peptide
      derived from antibody 21/6
<220> FEATURE:
<221> NAME/KEY: MOD_RES
<222> LOCATION: (1)
<223> OTHER INFORMATION: ACETYLATION

<400> SEQUENCE: 27

Tyr Tyr Gly Asn Tyr Gly Val Tyr Ala
 1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence:  Peptide
      derived from antibody 21/6

<400> SEQUENCE: 28

Tyr Tyr Gly Asn Tyr Gly Val Tyr Ala
 1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide pressinoic acid

<400> SEQUENCE: 29

Cys Tyr Phe Gln Asn Cys
 1               5

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Peptides
      derived from first domain of VCAM-1
<220> FEATURE:
<221> NAME/KEY: MOD_RES
<222> LOCATION: (1)
```

<223> OTHER INFORMATION: ACETYLATION

<400> SEQUENCE: 30

Pro Val Ser Phe Gly Asn Glu His Ser Tyr Leu
 1               5                  10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Peptide
      derived from first domain of VCAM-1

<400> SEQUENCE: 31

Cys Gly Phe Gly Asn Glu His Ser Tyr Cys
 1               5                  10

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Cyclic
      peptide derived from VCAM-1

<400> SEQUENCE: 32

Cys Phe Gly Asn Glu His Ser Cys
 1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 33

Glu Ser Pro Phe Phe Ser Trp Arg Thr Gln
 1               5                  10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Peptide
      derived from first domain of VCAM-1

<400> SEQUENCE: 34

Ser Trp Arg Thr Gln Ile Asp Ser Pro Leu
 1               5                  10

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Cyclic
      peptide derived from VCAM-1

<400> SEQUENCE: 35

Cys Arg Thr Gln Ile Asp Ser Cys
 1               5

<210> SEQ ID NO 36
<211> LENGTH: 10

```
<212> TYPE: PRT
<213> ORGANISM: Artificial Sequence
<220> FEATURE:
<223> OTHER INFORMATION: Description of Artificial Sequence: Cyclic
      peptide derived from first domain of VCAM-1

<400> SEQUENCE: 36

Cys Gly Arg Thr Gln Ile Asp Ser Gly Cys
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 37

Ile Asp Ser Pro Leu Asn Gly Lys Val Thr
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 38

Asn Gly Lys Val Thr Asn Glu Gly Thr Thr
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 39

Asn Glu Gly Thr Thr Ser Thr Leu Thr Met
 1               5                  10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 40

Ser Thr Leu Thr Met Asn Pro Val Ser Phe
 1               5                  10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Peptide
      derived from VCAM-1
<220> FEATURE:
<221> NAME/KEY: MOD_RES
<222> LOCATION: (1)
<223> OTHER INFORMATION: ACETYLATION
```

```
<400> SEQUENCE: 41

Glu Gly Tyr Tyr Gly Asn Tyr Gly Ala Ala Ala
 1               5                  10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Peptide
      derived from VCAM-1
<220> FEATURE:
<221> NAME/KEY: MOD_RES
<222> LOCATION: (1)
<223> OTHER INFORMATION: ACETYLATION

<400> SEQUENCE: 42

Glu Gly Tyr Tyr Gly Asn Tyr Gly Ala Tyr Ala
 1               5                  10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Peptide
      derived from VCAM-1
<220> FEATURE:
<221> NAME/KEY: MOD_RES
<222> LOCATION: (1)
<223> OTHER INFORMATION: ACETYLATION

<400> SEQUENCE: 43

Glu Gly Tyr Tyr Gly Asn Tyr Gly Gly Tyr Ala
 1               5                  10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Peptide
      derived from VCAM-1
<220> FEATURE:
<221> NAME/KEY: MOD_RES
<222> LOCATION: (1)
<223> OTHER INFORMATION: ACETYLATION

<400> SEQUENCE: 44

Glu Gly Tyr Tyr Gly Asn Tyr Ala Val Tyr Ala
 1               5                  10

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Peptide
      derived from VCAM-1
<220> FEATURE:
<221> NAME/KEY: MOD_RES
<222> LOCATION: (1)
<223> OTHER INFORMATION: ACETYLATION

<400> SEQUENCE: 45

Tyr Tyr Gly Asn Tyr Gly Val Tyr Ala
 1               5

<210> SEQ ID NO 46
<211> LENGTH: 6
```

-continued

```
<212> TYPE: PRT
<213> ORGANISM: Artificial Sequence
<220> FEATURE:
<223> OTHER INFORMATION: Description of Artificial Sequence: Cyclic
      peptide derived from VCAM-1

<400> SEQUENCE: 46

Cys Tyr Phe Gly Asn Cys
 1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence:
      N-acetylated peptide derived from VCAM-1
<220> FEATURE:
<221> NAME/KEY: MOD_RES
<222> LOCATION: (1)
<223> OTHER INFORMATION: ACETYLATION

<400> SEQUENCE: 47

Cys Tyr Phe Gly Asn Cys
 1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide derived from VCAM-1

<400> SEQUENCE: 48

Cys Tyr Phe Gln Tyr Cys
 1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide derived from VCAM-1

<400> SEQUENCE: 49

Cys Gly Phe Gly Tyr Cys
 1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide derived from VCAM-1

<400> SEQUENCE: 50

Cys Tyr Tyr Gly Tyr Cys
 1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide derived from VCAM-1
```

```
<400> SEQUENCE: 51

Cys Tyr Tyr Gly Gln Cys
 1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence:
      N-acetylated peptide derived from VCAM-1
<220> FEATURE:
<221> NAME/KEY: MOD_RES
<222> LOCATION: (1)
<223> OTHER INFORMATION: ACETYLATION

<400> SEQUENCE: 52

Tyr Tyr Gly Gln Cys
 1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide derived from VCAM-1

<400> SEQUENCE: 53

Cys Tyr Tyr Gly Ala Cys
 1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Peptide
      derived from VCAM-1
<220> FEATURE:
<221> NAME/KEY: MOD_RES
<222> LOCATION: (1)
<223> OTHER INFORMATION: ACETYLATION

<400> SEQUENCE: 54

Tyr Tyr Gly Ala Cys
 1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 55

Cys Ala Tyr Gly Asn Cys
 1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Peptide
      derived from VCAM-1
<220> FEATURE:
<221> NAME/KEY: MOD_RES
<222> LOCATION: (1)
```

```
<223> OTHER INFORMATION: ACETYLATION

<400> SEQUENCE: 56

Ala Tyr Gly Asn Cys
 1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 57

Cys Tyr Ala Gly Asn Cys
 1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence:
      N-acetylated Peptide derived from VCAM-1
<220> FEATURE:
<221> NAME/KEY: MOD_RES
<222> LOCATION: (1)
<223> OTHER INFORMATION: ACETYLATION

<400> SEQUENCE: 58

Tyr Ala Gly Asn Cys
 1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 59

Cys Tyr Tyr Glu Asn Cys
 1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Peptide
      derived from VCAM-1
<220> FEATURE:
<221> NAME/KEY: MOD_RES
<222> LOCATION: (1)
<223> OTHER INFORMATION: ACETYLATION

<400> SEQUENCE: 60

Tyr Tyr Glu Asn Cys
 1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Peptide
      derived from VCAM-1
```

```
<400> SEQUENCE: 61

Cys Tyr Tyr Gly Tyr Asn Cys
  1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence:
      N-acetylated peptide derived from VCAM-1
<220> FEATURE:
<221> NAME/KEY: MOD_RES
<222> LOCATION: (1)
<223> OTHER INFORMATION: ACETYLATION

<400> SEQUENCE: 62

Tyr Tyr Gly Tyr Asn Cys
  1               5

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 63

Cys Tyr Phe Gly Asn Glu His Ser Tyr Cys Gly
  1               5                  10

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: C-amidated
      peptide derived from VCAM-1
<220> FEATURE:
<221> NAME/KEY: MOD_RES
<222> LOCATION: (7)
<223> OTHER INFORMATION: AMIDATION

<400> SEQUENCE: 64

Glu Gly Tyr Tyr Gly Asn Tyr
  1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: C-amidated
      N-acetylated peptide derived from VCAM-1
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (9)
<223> OTHER INFORMATION: AMIDATION

<400> SEQUENCE: 65

Glu Gly Tyr Tyr Gly Asn Tyr Gly Val
  1               5

<210> SEQ ID NO 66
<211> LENGTH: 10
```

<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 66

Asn Pro Val Ser Phe Gly Asn Glu His Ser
 1               5                  10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Peptide
      derived from VCAM-1
<220> FEATURE:
<221> NAME/KEY: MOD_RES
<222> LOCATION: (1)
<223> OTHER INFORMATION: ACETYLATION

<400> SEQUENCE: 67

Thr Met Asn Pro Val Ser Phe
 1               5

<210> SEQ ID NO 68
<211> LENGTH: 12
<212> TYPE: PRT
<213> ORGANISM: Artificial Sequence
<220> FEATURE:
<221> NAME/KEY: MOD_RES
<222> LOCATION: (2)
<223> OTHER INFORMATION: This position is the D form of Tyr.
<220> FEATURE:
<221> NAME/KEY: MOD_RES
<222> LOCATION: (8)
<223> OTHER INFORMATION: This position is the D form of Tyr.
<220> FEATURE:
<223> OTHER INFORMATION: Description of Artificial Sequence: Dimeric
      peptide derived from VCAM-1

<400> SEQUENCE: 68

Ala Tyr Phe Gly Asn Cys Ala Tyr Phe Gly Asn Cys
 1               5                  10

<210> SEQ ID NO 69
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 69

Pro Val Ser Phe Glu Asn Glu His Ser Tyr Leu
 1               5                  10

<210> SEQ ID NO 70
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide derived from VCAM-1

<400> SEQUENCE: 70

Leu Thr Met Asn Pro Val Ser Phe
 1               5

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Dimeric
      peptide derived from VCAM-1

<400> SEQUENCE: 71

Ala Tyr Phe Gly Pro Cys Ala Tyr Phe Gly Pro Cys
 1               5                  10

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1
<220> FEATURE:
<221> NAME/KEY: MOD_RES
<222> LOCATION: (1)
<223> OTHER INFORMATION: ACETYLATION

<400> SEQUENCE: 72

Asn Pro Val Ser Phe Gly
 1               5

<210> SEQ ID NO 73
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: This position is the D form of Tyr.
<220> FEATURE:
<221> NAME/KEY: MOD_RES
<222> LOCATION: (6)
<223> OTHER INFORMATION: AMIDATION
<220> FEATURE:
<223> OTHER INFORMATION: Description of Artificial Sequence: Peptide
      derived from VCAM-1

<400> SEQUENCE: 73

Cys Tyr Tyr Glu Ala Cys
 1               5

<210> SEQ ID NO 74
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from antibody 21/6

<400> SEQUENCE: 74

Gly Tyr Tyr Gly Asn Cys
 1               5

<210> SEQ ID NO 75

```
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 75

Asn Pro Val Ser Phe
 1               5

<210> SEQ ID NO 76
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from antibody 21/6

<400> SEQUENCE: 76

Tyr Tyr Gly Asn Cys
 1               5

<210> SEQ ID NO 77
<211> LENGTH: 9
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (9)
<223> OTHER INFORMATION: AMIDATION
<220> FEATURE:
<223> OTHER INFORMATION: Description of Artificial Sequence: Peptide
      derived from antibody 21/6

<400> SEQUENCE: 77

Tyr Tyr Gly Asn Tyr Gly Val Tyr Ala
 1               5

<210> SEQ ID NO 78
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 78

Phe Gly Asn Glu His
 1               5

<210> SEQ ID NO 79
<211> LENGTH: 9
<212> TYPE: PRT
<213> ORGANISM: Artificial Sequence
<220> FEATURE:
```

```
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 79

Thr Leu Thr Met Asn Pro Val Ser Phe
  1               5

<210> SEQ ID NO 80
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1
<220> FEATURE:
<221> NAME/KEY: MOD_RES
<222> LOCATION: (1)
<223> OTHER INFORMATION: Position 1 is D form of Tyr

<400> SEQUENCE: 80

Tyr Phe Gly Asn Cys
  1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 81

Cys Tyr Tyr Gln Tyr Cys
  1               5

<210> SEQ ID NO 82
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 82

Pro Val Ser Phe
  1

<210> SEQ ID NO 83
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1; Cyclic

<400> SEQUENCE: 83
```

```
Met Asn Pro Val Ser Phe
 1               5
```

```
<210> SEQ ID NO 84
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Tyr
<220> FEATURE:
<223> OTHER INFORMATION: Description of Artificial Sequence: Peptide
      derived from VCAM-1

<400> SEQUENCE: 84
```

```
Cys Tyr Phe Gly Asn Cys
 1               5
```

```
<210> SEQ ID NO 85
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: Position 1 is D form of Asp
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1; Cyclic

<400> SEQUENCE: 85
```

```
Asp Phe Gly Asn Cys
 1               5
```

```
<210> SEQ ID NO 86
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from antibody 21/6

<400> SEQUENCE: 86
```

```
Tyr Tyr Gly Asn Tyr Cys
 1               5
```

```
<210> SEQ ID NO 87
<211> LENGTH: 10
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 87
```

```
Ser Thr Leu Thr Met Asn Pro Val Ser Phe
 1               5                   10
```

```
<210> SEQ ID NO 88
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Asp
<220> FEATURE:
<223> OTHER INFORMATION: Description of Artificial Sequence: Peptide
      derived from VCAM-1; Cyclic

<400> SEQUENCE: 88

Cys Asp Phe Gly Asn Cys
  1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1; Cyclic

<400> SEQUENCE: 89

Cys Tyr Phe Gly Pro Cys
  1               5

<210> SEQ ID NO 90
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: This position is the D form of Arg
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1; Cyclic

<400> SEQUENCE: 90

Arg Phe Gly Asn Cys
  1               5

<210> SEQ ID NO 91
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: This is the D form of Arg
<220> FEATURE:
<223> OTHER INFORMATION: Description of Artificial Sequence: Peptide
      derived from VCAM-1; Cyclic

<400> SEQUENCE: 91

Cys Arg Phe Gly Asn Cys
  1               5

<210> SEQ ID NO 92
<211> LENGTH: 5
<212> TYPE: PRT
<213> ORGANISM: Artificial Sequence
<220> FEATURE:
<221> NAME/KEY: MOD_RES
<222> LOCATION: (1)
```

```
<223> OTHER INFORMATION: This is the D form of Met
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1; Cyclic

<400> SEQUENCE: 92

Met Phe Gly Asn Cys
 1               5

<210> SEQ ID NO 93
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Met
<220> FEATURE:
<223> OTHER INFORMATION: Description of Artificial Sequence: Peptide
      derived from VCAM-1; Cyclic

<400> SEQUENCE: 93

Cys Met Phe Gly Asn Cys
 1               5

<210> SEQ ID NO 94
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: Position 1 is D form of Leu
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide is
      derived from VCAM-1

<400> SEQUENCE: 94

Leu Phe Gly Asn Cys
 1               5

<210> SEQ ID NO 95
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Leu
<220> FEATURE:
<223> OTHER INFORMATION: Description of Artificial Sequence: Peptide
      derived from VCAM-1; Cyclic

<400> SEQUENCE: 95

Cys Leu Phe Gly Asn Cys
 1               5

<210> SEQ ID NO 96
<211> LENGTH: 5
<212> TYPE: PRT
<213> ORGANISM: Artificial Sequence
<220> FEATURE:
<221> NAME/KEY: MOD_RES
<222> LOCATION: (1)
```

<223> OTHER INFORMATION: Position 1 is D form of Val
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide is
      derived from VCAM-1

<400> SEQUENCE: 96

Val Phe Gly Asn Cys
 1               5

<210> SEQ ID NO 97
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Val
<220> FEATURE:
<223> OTHER INFORMATION: Description of Artificial Sequence: Peptide is
      derived from VCAM-1; Cyclic

<400> SEQUENCE: 97

Cys Val Phe Gly Asn Cys
 1                   5

<210> SEQ ID NO 98
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: Position 1 is D form of Ser
<220> FEATURE:
<221> NAME/KEY: MOD_RES
<222> LOCATION: ()..)
<223> OTHER INFORMATION: ACETYLATION
<220> FEATURE:
<223> OTHER INFORMATION: Description of Artificial Sequence: Peptide
      derived from VCAM-1

<400> SEQUENCE: 98

Ser Phe Gly Asn Cys
 1               5

<210> SEQ ID NO 99
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Ser
<220> FEATURE:
<223> OTHER INFORMATION: Description of Artificial Sequence: Peptide
      derived from VCAM-1

<400> SEQUENCE: 99

Cys Ser Phe Gly Asn Cys
 1                   5

<210> SEQ ID NO 100
<211> LENGTH: 5
<212> TYPE: PRT
<213> ORGANISM: Artificial Sequence
<220> FEATURE:
<221> NAME/KEY: MOD_RES
<222> LOCATION: (1)

```
<223> OTHER INFORMATION: ACETYLATION
<220> FEATURE:
<223> OTHER INFORMATION: Description of Artificial Sequence: Peptide
      derived from VCAM-1

<400> SEQUENCE: 100

Asp Phe Gly Asn Cys
 1               5

<210> SEQ ID NO 101
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 101

Arg Phe Gly Asn Cys
 1               5

<210> SEQ ID NO 102
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 102

Met Phe Gly Asn Cys
 1               5

<210> SEQ ID NO 103
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 103

Leu Phe Gly Asn Cys
 1               5

<210> SEQ ID NO 104
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 104

Val Phe Gly Asn Cys
```

```
<210> SEQ ID NO 105
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence:Peptide derived
      from VCAM-1

<400> SEQUENCE: 105

Ser Phe Gly Asn Cys
  1               5

<210> SEQ ID NO 106
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: Position 1 is D form of Phe
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 106

Phe Phe Gly Asn Cys
  1               5

<210> SEQ ID NO 107
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Phe
<220> FEATURE:
<223> OTHER INFORMATION: Description of Artificial Sequence: Peptide
      derived from VCAM-1; Cyclic

<400> SEQUENCE: 107

Cys Phe Phe Gly Asn Cys
  1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 108

Cys Asp Phe Gly Asn Cys
  1               5

<210> SEQ ID NO 109
<211> LENGTH: 6
<212> TYPE: PRT
<213> ORGANISM: Artificial Sequence
<220> FEATURE:
```

```
<223> OTHER INFORMATION: Description of Artificial Sequence: Peptide
      derived from VCAM-1

<400> SEQUENCE: 109

Cys Arg Phe Gly Asn Cys
 1               5

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 110

Cys Met Phe Gly Asn Cys
 1               5

<210> SEQ ID NO 111
<211> LENGTH: 12
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Leu
<220> FEATURE:
<221> NAME/KEY: MOD_RES
<222> LOCATION: (8)
<223> OTHER INFORMATION: Position 8 is D form of Leu
<220> FEATURE:
<223> OTHER INFORMATION: Description of Artificial Sequence: Peptide
      derived from VCAM-1

<400> SEQUENCE: 111

Ala Leu Leu Asp Val Cys Ala Leu Leu Asp Val Cys
 1               5                  10

<210> SEQ ID NO 112
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Ile
<220> FEATURE:
<223> OTHER INFORMATION: Description of Artificial Sequence: Peptide
      derived from VCAM-1 or fibronectin

<400> SEQUENCE: 112

Ala Ile Leu Asp Val Cys
 1               5

<210> SEQ ID NO 113
<211> LENGTH: 12
<212> TYPE: PRT
<213> ORGANISM: Artificial Sequence
<220> FEATURE:
<221> NAME/KEY: MOD_RES
<222> LOCATION: (2,8)
<223> OTHER INFORMATION: Positions 2 and 8 are D form of Ile
<220> FEATURE:
<223> OTHER INFORMATION: Description of Artificial Sequence: Dimer
      peptide derived from VCAM-1 or fibronectin

<400> SEQUENCE: 113

Ala Ile Leu Asp Val Cys Ala Ile Leu Asp Val Cys
 1               5                  10
```

```
<210> SEQ ID NO 114
<211> LENGTH: 5
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Phe
<220> FEATURE:
<223> OTHER INFORMATION: Description of Artificial Sequence: Peptide
      derived from VCAM-1

<400> SEQUENCE: 114

Ala Phe Gly Asn Cys
 1               5

<210> SEQ ID NO 115
<211> LENGTH: 10
<212> TYPE: PRT
<213> ORGANISM: Artificial Sequence
<220> FEATURE:
<221> NAME/KEY: MOD_RES
<222> LOCATION: (2,7)
<223> OTHER INFORMATION: Positions 2 and 7 are D form of Phe
<220> FEATURE:
<223> OTHER INFORMATION: Description of Artificial Sequence: Peptide
      derived from VCAM-1

<400> SEQUENCE: 115

Ala Phe Gly Asn Cys Ala Phe Gly Asn Cys
 1               5                  10

<210> SEQ ID NO 116
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Leu
<220> FEATURE:
<223> OTHER INFORMATION: Description of Artificial Sequence: Peptide
      derived from VCAM-1

<400> SEQUENCE: 116

Ala Leu Leu Asp Val Cys
 1               5

<210> SEQ ID NO 117
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Ser
<220> FEATURE:
<221> NAME/KEY: MOD_RES
<222> LOCATION: (6)
<223> OTHER INFORMATION: AMIDATION
<220> FEATURE:
<223> OTHER INFORMATION: Description of Artificial Sequence: Peptide
      derived from VCAM-1

<400> SEQUENCE: 117

Cys Ser Phe Glu Asp Cys
 1               5

<210> SEQ ID NO 118
<211> LENGTH: 6
<212> TYPE: PRT
```

<213> ORGANISM: Artificial Sequence
<220> FEATURE:
<221> NAME/KEY: MOD_RES
<222> LOCATION: (2)
<223> OTHER INFORMATION: Position 2 is D form of Ser
<220> FEATURE:
<223> OTHER INFORMATION: Description of Artificial Sequence: Peptide is
      derived from VCAM-1; Cyclic

<400> SEQUENCE: 118

Cys Ser Phe Glu Asp Cys
 1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1; Cyclic

<400> SEQUENCE: 119

Cys Ser Phe Glu Asp Cys
 1               5

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 120

Cys Leu Phe Gly Asn Cys
 1               5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 121

Cys Val Phe Gly Asn Cys
 1               5

<210> SEQ ID NO 122
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Tyr
<220> FEATURE:
<223> OTHER INFORMATION: Description of Artificial Sequence: Peptide
      derived from VCAM-1

<400> SEQUENCE: 122

Cys Tyr Tyr Glu Ala Cys
 1               5

<210> SEQ ID NO 123
<211> LENGTH: 12
<212> TYPE: PRT
<213> ORGANISM: Artificial Sequence
<220> FEATURE:

```
<223> OTHER INFORMATION: Description of Artificial Sequence: Peptide
      derived from VCAM-1 or antibody 21/6

<400> SEQUENCE: 123

Ala Tyr Tyr Glu Asn Cys Ala Tyr Tyr Glu Asn Cys
 1               5                  10

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1 or antibody 21/6

<400> SEQUENCE: 124

Ser Tyr Tyr Glu Asn Cys
 1               5

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Dimeric
      peptide derived from VCAM-1 or antibody 21/6

<400> SEQUENCE: 125

Ser Tyr Tyr Glu Asn Cys Ser Tyr Tyr Glu Asn Cys
 1               5                  10

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1 or antibody 21/6

<400> SEQUENCE: 126

Cys Ser Phe Gly Asn Cys
 1               5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1 or antibody 21/6

<400> SEQUENCE: 127

Cys Tyr Tyr Glu Ala Cys
 1               5

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1 or antibody 21/6
<220> FEATURE:
<221> NAME/KEY: MOD_RES
<222> LOCATION: (2)
<223> OTHER INFORMATION: Position 2 is D form of Tyr

<400> SEQUENCE: 128

Cys Tyr Tyr Gly Ala Cys
```

<210> SEQ ID NO 129
<211> LENGTH: 6
<212> TYPE: PRT
<213> ORGANISM: Artificial Sequence
<220> FEATURE:
<221> NAME/KEY: MOD_RES
<222> LOCATION: (6)
<223> OTHER INFORMATION: AMIDATION
<220> FEATURE:
<223> OTHER INFORMATION: Description of Artificial Sequence: Peptide
      derived from VCAM-1

<400> SEQUENCE: 129

Cys Tyr Tyr Glu Asn Cys
 1               5

<210> SEQ ID NO 130
<211> LENGTH: 6
<212> TYPE: PRT
<213> ORGANISM: Artificial Sequence
<220> FEATURE:
<221> NAME/KEY: MOD_RES
<222> LOCATION: (4)
<223> OTHER INFORMATION: Position 4 is D form of Asp
<220> FEATURE:
<223> OTHER INFORMATION: Description of Artificial Sequence: Peptide
      derived from VCAM-1

<400> SEQUENCE: 130

Cys Tyr Tyr Asp Ala Cys
 1               5

<210> SEQ ID NO 131
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Tyr
<220> FEATURE:
<223> OTHER INFORMATION: Description of Artificial Sequence: Peptide
      derived from VCAM-1

<400> SEQUENCE: 131

Ala Tyr Phe Gly Asn Cys
 1               5

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 132

Ala Tyr Phe Gly Asn Cys Ala Tyr Phe Gly Asn Cys
 1               5                  10

<210> SEQ ID NO 133
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Tyr
<220> FEATURE:

```
<223> OTHER INFORMATION: Description of Artificial Sequence: Peptide
      derived from VCAM-1

<400> SEQUENCE: 133

Ala Tyr Tyr Glu Ala Cys
 1               5

<210> SEQ ID NO 134
<211> LENGTH: 6
<212> TYPE: PRT
<213> ORGANISM: Artificial Sequence
<220> FEATURE:
<221> NAME/KEY: MOD_RES
<222> LOCATION: (6)
<223> OTHER INFORMATION: AMIDATION
<220> FEATURE:
<223> OTHER INFORMATION: Description of Artificial Sequence: Peptide
      derived from VCAM-1

<400> SEQUENCE: 134

Cys Tyr Tyr Gly Ala Cys
 1               5

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 135

Cys Tyr Tyr Gly Gly Cys
 1               5

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 136

Cys Tyr Tyr Asp Ala Cys
 1               5

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 137

Cys Tyr Tyr Ala Ala Cys
 1               5

<210> SEQ ID NO 138
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Tyr
<220> FEATURE:
<223> OTHER INFORMATION: Description of Artificial Sequence: Peptide
      derived from VCAM-; Cyclic
```

```
<400> SEQUENCE: 138

Cys Tyr Tyr Glu Asn Cys
 1               5

<210> SEQ ID NO 139
<211> LENGTH: 6
<212> TYPE: PRT
<213> ORGANISM: Artificial Sequence
<220> FEATURE:
<221> NAME/KEY: MOD_RES
<222> LOCATION: (4)
<223> OTHER INFORMATION: Position 4 is D form of Glu
<220> FEATURE:
<223> OTHER INFORMATION: Description of Artificial Sequence: Peptide
      derived from VCAM-1; Cyclic

<400> SEQUENCE: 139

Cys Tyr Tyr Glu Ala Cys
 1               5

<210> SEQ ID NO 140
<211> LENGTH: 12
<212> TYPE: PRT
<213> ORGANISM: Artificial Sequence
<220> FEATURE:
<221> NAME/KEY: MOD_RES
<222> LOCATION: (2,8)
<223> OTHER INFORMATION: Positions 2 and 8 are D form of Tyr
<220> FEATURE:
<223> OTHER INFORMATION: Description of Artificial Sequence:Cyclic
      peptide derived from VCAM-1

<400> SEQUENCE: 140

Ala Tyr Tyr Glu Ala Cys Ala Tyr Tyr Glu Ala Cys
 1               5                  10

<210> SEQ ID NO 141
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Tyr
<220> FEATURE:
<223> OTHER INFORMATION: Description of Artificial Sequence: Peptide
      derived from VCAM-1

<400> SEQUENCE: 141

Ala Tyr Tyr Glu Asn Cys
 1               5

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 142

Ala Tyr Phe Gly Pro Cys
 1               5

<210> SEQ ID NO 143
<211> LENGTH: 12
<212> TYPE: PRT
<213> ORGANISM: Artificial Sequence
<220> FEATURE:
```

-continued

<223> OTHER INFORMATION: Description of Artificial Sequence: Dimeric
      peptide derived from VCAM-1

<400> SEQUENCE: 143

Ala Asp Phe Gly Asn Cys Ala Asp Phe Gly Asn Cys
 1               5                  10

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Dimeric
      peptide derived from VCAM-1

<400> SEQUENCE: 144

Ala Tyr Tyr Gly Tyr Asn Cys Ala Tyr Tyr Gly Tyr Asn Cys
 1               5                  10

<210> SEQ ID NO 145
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<223> OTHER INFORMATION: Description of Artificial Sequence: Peptide
      derived from VCAM-1

<400> SEQUENCE: 145

Tyr Phe Gly Pro Cys
 1               5

<210> SEQ ID NO 146
<211> LENGTH: 6
<212> TYPE: PRT
<213> ORGANISM: Artificial Sequence
<220> FEATURE:
<221> NAME/KEY: MOD_RES
<222> LOCATION: (5)
<223> OTHER INFORMATION: Position 5 is D form of Asp
<220> FEATURE:
<223> OTHER INFORMATION: Description of Artificial Sequence: Peptide
      derived from VCAM-1

<400> SEQUENCE: 146

Cys Tyr Tyr Gly Asp Cys
 1               5

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1; Cyclic

<400> SEQUENCE: 147

Cys Tyr Tyr Gly Glu Cys
 1               5

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1; Cyclic

<400> SEQUENCE: 148

Cys Tyr Tyr Gly Asp Cys
 1               5

<210> SEQ ID NO 149
<211> LENGTH: 6
<212> TYPE: PRT
<213> ORGANISM: Artificial Sequence
<220> FEATURE:
<221> NAME/KEY: MOD_RES
<222> LOCATION: (5)
<223> OTHER INFORMATION: Position 5 is D form of Glu
<220> FEATURE:
<223> OTHER INFORMATION: Description of Artificial Sequence: Peptide
      derived from VCAM-1; Cyclic

<400> SEQUENCE: 149

Cys Tyr Tyr Gly Glu Cys
 1               5

<210> SEQ ID NO 150
<211> LENGTH: 12
<212> TYPE: PRT
<213> ORGANISM: Artificial Sequence
<220> FEATURE:
<221> NAME/KEY: MOD_RES
<222> LOCATION: (2,8)
<223> OTHER INFORMATION: Positions 2 and 8 are D form of Tyr
<220> FEATURE:
<223> OTHER INFORMATION: Description of Artificial Sequence: Dimeric
      peptide derived from VCAM-1

<400> SEQUENCE: 150

Ala Tyr Tyr Gly Ala Cys Ala Tyr Tyr Gly Ala Cys
 1               5                  10

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 151

Ala Tyr Tyr Gly Tyr Asn Cys
 1               5

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 152

Ala Tyr Phe Gly Asn Cys
 1               5

<210> SEQ ID NO 153
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Tyr
<220> FEATURE:

<223> OTHER INFORMATION: Description of Artificial Sequence: Peptide
      derived from VCAM-1

<400> SEQUENCE: 153

Ala Tyr Tyr Gly Ala Cys
 1               5

<210> SEQ ID NO 154
<211> LENGTH: 12
<212> TYPE: PRT
<213> ORGANISM: Artificial Sequence
<220> FEATURE:
<221> NAME/KEY: MOD_RES
<222> LOCATION: (2,8)
<223> OTHER INFORMATION: Positions 2 and 8 are D form of Tyr
<220> FEATURE:
<223> OTHER INFORMATION: Description of Artificial Sequence: Dimeric
      peptide derived from VCAM-1

<400> SEQUENCE: 154

Ala Tyr Tyr Glu Asn Cys Ala Tyr Tyr Glu Asn Cys
 1               5                  10

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Peptide
      derived from VCAM-1

<400> SEQUENCE: 155

Ala Asp Phe Gly Asn Cys
 1               5

<210> SEQ ID NO 156
<211> LENGTH: 6
<212> TYPE: PRT
<213> ORGANISM: Artificial Sequence
<220> FEATURE:
<221> NAME/KEY: MOD_RES
<222> LOCATION: (6)
<223> OTHER INFORMATION: AMIDATION
<220> FEATURE:
<221> NAME/KEY: MOD_RES
<222> LOCATION: (2)
<223> OTHER INFORMATION: Position 2 is D form of Tyr
<220> FEATURE:
<223> OTHER INFORMATION: Description of Artificial Sequence: Peptide
      derived from VCAM-1

<400> SEQUENCE: 156

Cys Tyr Tyr Gly Ala Cys
 1               5

<210> SEQ ID NO 157
<211> LENGTH: 6
<212> TYPE: PRT
<213> ORGANISM: Artificial Sequence
<220> FEATURE:
<221> NAME/KEY: MOD_RES
<222> LOCATION: (2)
<223> OTHER INFORMATION: Position 2 is D form of Tyr
<220> FEATURE:
<221> NAME/KEY: MOD_RES
<222> LOCATION: (6)
<223> OTHER INFORMATION: AMIDATION
<220> FEATURE:
<223> OTHER INFORMATION: Description of Artificial Sequence: Peptide
      derived from VCAM-1

<400> SEQUENCE: 157

Cys Tyr Tyr Glu Asn Cys
 1               5

<210> SEQ ID NO 158
<211> LENGTH: 4
<212> TYPE: PRT
<213> ORGANISM: Artificial Sequence
<220> FEATURE:
<223> OTHER INFORMATION: Description of Artificial Sequence:  Peptide
      derived from VCAM-1 or antibody 21/6

<400> SEQUENCE: 158

Tyr Tyr Gly Asn
 1

<210> SEQ ID NO 159
<211> LENGTH: 4
<212> TYPE: PRT
<213> ORGANISM: Artificial Sequence
<220> FEATURE:
<223> OTHER INFORMATION: Description of Artificial Sequence: Peptide
      derived from VCAM-1 or 21/6 antibody

<400> SEQUENCE: 159

Tyr Phe Gly Asn
 1

<210> SEQ ID NO 160
<211> LENGTH: 4
<212> TYPE: PRT
<213> ORGANISM: Artificial Sequence
<220> FEATURE:
<223> OTHER INFORMATION: Description of Artificial Sequence: Peptide
      derived from VCAM-1 or 21/6 antibody

<400> SEQUENCE: 160

Phe Gly Asn Glu
 1

<210> SEQ ID NO 161
<211> LENGTH: 4
<212> TYPE: PRT
<213> ORGANISM: Artificial Sequence
<220> FEATURE:
<223> OTHER INFORMATION: Description of Artificial Sequence: Peptide
      derived from VCAM-1 or 21/6 antibody

<400> SEQUENCE: 161

Tyr Gly Asn Glu
 1

<210> SEQ ID NO 162
<211> LENGTH: 4
<212> TYPE: PRT
<213> ORGANISM: Artificial Sequence
<220> FEATURE:
<223> OTHER INFORMATION: Description of Artificial Sequence: Peptide
      derived from VCAM-1 or 21/6 antibody

<400> SEQUENCE: 162

Phe Glu Asn Glu
 1

<210> SEQ ID NO 163
<211> LENGTH: 8
<212> TYPE: PRT
<213> ORGANISM: Artificial Sequence
<220> FEATURE:

```
<223> OTHER INFORMATION: Description of Artificial Sequence: Peptide
      derived from CDR3 region of 21/6 antibody

<400> SEQUENCE: 163

Tyr Tyr Gly Asn Tyr Gly Val Tyr
  1               5
```

INHIBITORS OF LEUKOCYTE ADHESION

This application is a continuation-in-part of U.S. patent application Ser. No. 08/273,055 filed July 11, 1994, now abandoned, which application is incorporated herein by reference in its entirety.

BACKGROUND OF THE INVENTION

FIELD OF THE INVENTION

This invention relates to inhibitors of leukocyte adhesion. In particular, it relates to oligopeptides that block adhesion mediated by VLA-4.

REFERENCES

The following publications, patents and patent applications are cited in this application as superscript numbers:

1 Hemler and Takada, European Patent Application Publication No. 330,506, published Aug. 30, 1989
2 Elices, et al., *Cell*, 60:577–584 (1990)
3 Springer, *Nature*, 346:425–434 (1990)
4 Osborn, *Cell*, 62:3–6 (1990)
5 Vedder, et al., *Surgery*, 106:509 (1989)
6 Pretolani, et al., *J. Exp. Med.*, 180:795 (1994)
7 Abraham, et al., *J. Clin. Invest.*, 93:776 (1994)
8 Mulligan, et al., *J. Immunology*, 150:2407 (1993)
9 Cybulsky, et al., *Science*, 251:788 (1991)
10 Li, et al., *Arterioslcer. Thromb.*, 13:197 (1993)
11 Sasseville, et al., *Am. J. Path.*, 144:27 (1994)
12 Yang, et al., *Proc. Nat. Acad. Science (USA)*, 90:10494 (1993)
13 Burkly, et al., *Diabetes*, 43:529 (1994)
14 Baron, et al., *J. Clin. Invest.*, 93:1700 (1994)
15 Hamann, et al., *J. Immunology*, 152:3238 (1994)
16 Yednock, et al., *Nature*, 356:63 (1992)
17 Baron, et al., *J. Exp. Med.*, 177:57 (1993)
18 van Dinther-Janssen, et al., *J. Immunology*, 147:4207 (1991)
19 van Dinther-Janssen, et al., *Annals. Rheumatic Dis.*, 52:672 (1993)
20 Elices, et al., *J. Clin. Invest.*, 93:405 (1994)
21 Postigo, et al., *J. Clin. Invest.*, 89:1445 (1991)
22 Paul, et al., *Transpl. Proceed.*, 25:813 (1993)
23 Okarhara, et al., *Can. Res.*, 54:3233 (1994)
24 Paavonen, et al., *Int. J. Can.*, 58:298 (1994)
25 Schadendorf, et al., *J. Path.*, 170:429 (1993)
26 Bao, et al., *Diff.*, 52:239 (1993)
27 Lauri, et al., *British J. Cancer*, 68:862 (1993)
28 Kawaguchi, et al., *Japanese J. Cancer Res.*, 83:1304 (1992)
29 Sambrook, et al., *Molecular Cloning, A Laboratory Manual*, Cold Spring Harbor Press, Cold Spring Harbor, N.Y. (1982)
30 Matteucci, et al., *J. Am. Chem. Soc.* 103:3185 (1981)
31 Robey, et al., *Anal. Biochem.*, 177:373–377 (1989)
32 Robey, et al., U.S. Pat. No. 5,066,716, issued Nov. 19, 1991
33 International Patent Application Publication No. WO 91/05038
34 Verhoef, et al., *Eur. J. Drug Metab. Pharmacokin.*, 11:291–302 (1986)
35 Langer, *Science*, 249:1527–1533 (1990)
36 Szoka et al., *Ann. Rev. Biophys. Bioeng.*, 9:467 (1980)
37 Papahadjopoulos, et al., U.S. Pat. No. 4,235,871, issued Nov. 15, 1980
38 Geho, et al., U.S. Pat. No. 4,501,728, issued Feb. 26, 1985
39 Allen, U.S. Pat. No. 4,837,028, issued Jun. 6, 1989
40 Wayner and Kovach, *J. Cell Biol.*, 116:489–497 (1992)
41 Vonderheide, et al., *J. Cell Biol.*, 125:215–222 (1994)
42 *J. Cell. Biol.*, 117:461–470 (1992)
43 *J. Cell. Biol.*, 117:659–670 (1992)

All of the above publications, patents and patent applications are herein incorporated by reference in their entirety to the same extent as if each individual publication, patent or patent application was specifically and individually indicated to be incorporated by reference in its entirety.

State of the Art

VLA-4 (also referred to as $\alpha 4\beta 1$ integrin and CD49d/CD29), first identified by Hemler and Takada[1] is a member of the $\beta 1$ integrin family of cell surface receptors, each of which comprises two subunits, an $\alpha$ chain and a $\beta$ chain. VLA-4 contains an $\alpha 4$ chain and a $\beta 1$ chain. There are at least nine $\beta 1$ integrins, all sharing the same $\beta 1$ chain and each having a distinct $\alpha$ chain. These nine receptors all bind a different complement of the various cell matrix molecules, such as fibronectin, laminin, and collagen. VLA-4, for example, binds to fibronectin. VLA-4 is unique among al integrins in that it also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently.[2]

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder et al.[5]). Other inflammatory conditions mediated by an adhesion mechanism include, by way of example, asthma[6-8], Alzheimer's disease, atherosclerosis[9-10], AIDS dementia[11], diabetes[12-14], inflammatory bowel disease[15], multiple sclerosis[16-17], rheumatoid arthritis[18-21], tissue transplantation[22] and tumor metastasis[23-28].

Despite these advances in the understanding of leukocyte adhesion, the prior art lacks small, peptidic inhibitors of adhesion useful in the treatment of inflammatory brain diseases and other inflammatory conditions. The present invention addresses these and other needs.

SUMMARY OF THE INVENTION

This invention provides compositions comprising peptides which, in monomer form, comprise from about 4 to about 13 amino acid residues, preferably from about 6 to about 10, which inhibit cellular adhesion mediated by VLA-4, for example, binding of VCAM-1 to VLA-4. The peptides may be either monomeric or dimeric and comprise peptides having a binding affinity to VLA-4 as expressed by an $IC_{50}$ of about 50 $\mu$M or less (measured as per Example 10 below), which peptides are selected from the group consisting of peptides defined by the formula $[R^1\text{-Y/F-G/E-}R^2]_n$ and peptides of the formula R-PVSF-R' where R and R' are independently peptide sequences of from 0 to 7 with the proviso that the sum of amino acid residues in R+R' is no more than 9, $R^1$ is a peptide sequence of from 0 to 6 amino acid residues and $R^2$ is a peptide sequence of from 1 to 7 amino acid residues with the proviso that the sum of amino acid residues in $R^1+R^2$ is from 2 to 11, and n is an integer equal to 1 or 2 wherein one or more of the amino acid residues in said peptides are optionally D-amino acid residues, further wherein the N-terminus of said peptide is optionally modified by linkage of the amine to a group of the formula $R_4$—CO— wherein, $R_4$ is hydrogen, lower alkyl, cycloalkyl, aryl, arylalkyl, or $R_5O$— where $R_5$ is lower alkyl, cycloalkyl, aryl and arylalkyl; and still further wherein the C-terminus of said peptide is optionally modified by linkage of the carbonyl [C(O)] to a group selected from —O—$R_6$ and

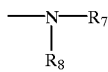

wherein $R_6$ is lower alkyl, cycloalkyl, aryl or arylalkyl and $R_7$ and $R_8$ are the same or different and are hydrogen, lower alkyl, cycloalkyl, aryl, or arylalkyl.

Peptides as defined by the formulas set forth above which have an $IC_{50}$ of about 50 $\mu$M or less (as per Example 6 below) include SEQ ID NOs. 4, 9, 12, 15, 17, 22, 31, 32, 40, 41, 42, 43, 45, 52, 54, 60, 62, 63, 71, 94, 96, 123, 124, 125, 133, 140, 142, 144, 150, and 154.

In some embodiments, the peptides are dimeric. The peptides may, for instance, comprise a C residue at the C-terminus. Preferred peptides include SEQ ID Nos. 71, 123, 125, 140, 144, 150 and 154.

This invention also provides pharmaceutical compositions comprising a pharmaceutically acceptable carrier and a therapeutically effective amount of one or more of the peptides of the invention. The pharmaceutical compositions may be used to inhibit adhesion of leukocytes to endothelial cells, for instance, in treating an inflammatory disease in a patient such as asthma, Alzheimer's disease, atherosclerosis, AIDS dementia, diabetes, inflammatory bowel disease, rheumatoid arthritis, tissue transplantation, tumor metastasis and myocardial ischemia. The compositions can also be administered for the treatment of inflammatory brain disorders, such as multiple sclerosis.

Definitions

The terms "peptide", "oligopeptide" or "polypeptide" are used to designate a series of amino acids residues or amino acid mimetics connected one to the other typically between the alpha-amino and alpha-carboxy groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification does not destroy the biological activity of the polypeptides as herein described.

An oligopeptide or peptide as used herein refers to a chain of at least about 4 residues, preferably at least about 8. The peptides are usually fewer than about 25 residues, more usually fewer than about 20 and preferably less than about 15. The peptides will typically range between about 8 and 10 residues.

The nomenclature used to describe peptide compounds follows the conventional practice wherein the amino group is presented to the left (the N-terminus) and the carboxyl group to the right (the C-terminus) of each amino acid residue. In the formulas representing selected specific embodiments of the present invention, the amino- and carboxyl-terminal groups, although not specifically shown, are in the form they would assume at physiologic pH values, unless otherwise specified. In the amino acid structures, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G.

The term "cyclic" refers to peptides in which the N-terminal residue is linked to the C-terminal residue either directly or through an intermediate. Examples of links between the two residues include disulfide bonds and thio-ether linkages as described below.

The term "dimer" refers to peptides in which the C-terminal residue of one oligopeptide is linked to the C-terminal residue of another oligopeptide directly or through an intermediate. An example of a link between the two residues include disulfide bonds as described below.

The term "isolated" or "isolate" refers to material which is substantially or essentially free from components which normally accompany it as found in its native state. Thus, the peptides of this invention do not contain materials normally associated with their in situ environment.

The term "residue" refers to an amino acid or amino acid mimetic incorporated in a peptide by an peptide bond or peptide bond mimetic.

The term "alkyl" as used herein means a branched or unbranched, saturated or unsaturated, monovalent or divalent, hydrocarbon radical having from 1 to 20 carbon atoms, including but not limited to lower alkyls of 1–10 carbon atoms such as methyl, ethyl, n-propyl, butyl (i.e., n-butyl, iso-butyl, sec-butyl and t-butyl), n-hexyl, and the like. This definition and the definitions below apply both when the term is used alone and when it is used as part of a compound term, such as "arylalkyl" and the like.

The term "acyl" as used herein refers to an carbonyl radical (CO) to which is appended an alkyl group, especially a lower alkyl group. Examples include radicals such as acetyl, propionyl and the like.

The term "cycloalkyl" as used herein refers to an aliphatic ring having 3 to 7 carbon atoms including, but not limited to, cyclopropyl, cylcobutyl, cyclopentyl, cyclohexyl and cycloheptyl. Preferred cycloalkyls include cyclopropyl, cyclopentyl, and cyclohexyl.

The term "aryl" as used herein refers to a monocyclic or polycyclic carbon ring system having from 6 to 14 carbon atoms including, but not limited to, phenyl, naphthyl, and the like. Preferred aryls include phenyl and naphthyl. Any of the aryl groups described herein may be optionally substituted with halogen atoms (i.e., fluoro, chloro, bromo and iodo), or other groups such as nitro, carboxyl, lower alkyl, lower alkoxy (O-lower alkyl), acyl, cycloalkyl, and the like.

BRIEF DESCRIPTION OF THE DRAWINGS

FIG. 1 shows the results of experiments measuring the ability of immobilized peptides of the invention to promote adhesion of Jurkat cells in the presence and absence of an anti-VLA-4 antibody.

FIG. 2 shows the results of experiments demonstrating the ability of peptides of the invention to block adhesion of soluble VCAM-1-IgG conjugates to Jurkat cells.

DESCRIPTION OF THE PREFERRED EMBODIMENTS

This invention provides oligopeptides which comprise adhesion signal sequences recognized by VLA-4. Thus, the peptides can be used to block VLA-4-mediated adhesion and inhibit immunopathologies associated with this adhesion.

The invention is based, in part, upon sequence analysis of 5 monoclonal antibodies against α4 integrin that inhibit VLA-4 binding to VCAM-1. This analysis revealed a short consensus stretch of amino acids within the heavy chain CDR3 of these antibodies. Three of the anti-α4 antibodies contain YGN . . . Y, while the fourth contains FGN . . . Y, (Y is typically considered to be a conservative amino acid substitution for F). The sequence of the fifth antibody is completely unrelated. Since the heavy chain CDR3 is the most variable region of an antibody molecule, the chances of obtaining this sequence at random in four separate antibodies is extremely remote. These sequences share homology with sequences within domain 1 of VCAM-1, FGN . . . Y, as well. In addition, sequences derived from other regions of domain 1 of VCAM-1 also block interaction between VCAM-1 and VLA-4. One example of a known adhesion signal from domain 1 is QIDS (Vonderheide, et al.,[41]).

The peptides of the invention thus comprise sequences derived from the sequences of the anti-VLA-4 antibodies noted above or from domains of VCAM-1. These sequences present adhesion signals which allow the peptides to inhibit VLA-4 mediated adhesion in vivo, for instance by binding VLA-4 thereby disrupting the binding of VLA-4 to VCAM-1. Preferred adhesion signal sequences are derived from the sequences YYGN (SEQ ID NO: 158), YFGN (SEQ ID NO: 159), FGNE (SEQ ID NO: 160), YGNE (SEQ ID NO: 161) or FENE (SEQ ID NO: 162). Peptides incorporating these sequences and their analogs, when appropriately presented, inhibit the binding of protein VCAM-1 to cells that express VLA-4, as demonstrated below.

The affinity of the peptides of the invention for the VLA-4 binding site related to VCAM-1 binding may be determined using the assay described in Example 10, below. The $IC_{50}$ values of the peptides of the invention, as determined by this assay, are generally below about 600 μM, preferably below about 100 μM, and more preferably less than about 5 μM. Dimeric peptides of the invention sometimes have better affinity than linear peptides.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols.

Peptides bound to a polymer support may be prepared by sequential coupling of individual amino acid derivatives by standard techniques (See, e.g., Stewart and Young, *Solid Phase Peptide Synthesis* (1984), Pierce Chemical Co., Rockford, Ill.). Cleavage of the peptide product from the polymer support may be accomplished in a variety of ways dependent upon the type of resin used and the chemical linkage between the peptide and the resin. If, for example, the resin is derived from a polymerized p-alkoxybenzyl alcohol derivative, then cleavage of the peptide-resin linkage may be carried out using a strong acid such as trifluoroacetic acid. Alternatively, if the peptide is synthesized on a polystyrene resin, the cleavage can be accomplished using liquid hydrogen fluoride. If desired, additives such as phenol, anisole and ethanedithiol may be added to the reaction. The crude product thus obtained may be further purified using chromatographic or other methods of chemical purification well known to those of skill in the art.

The peptides may also be prepared by the sequential coupling of amino acid derivatives in solution without the use of polymer resin or other solid supports. The methods useful for solution phase peptide synthesis are well documented in the chemical literature and are known to those skilled in the art.

In the peptides of the invention carbon atoms bonded to four nonidentical substituents are asymmetric. Accordingly, the compounds may exist as diastereoisomers, enantiomers or mixtures thereof. The syntheses described above may employ racemates, enantiomers or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present in a peptide, may be in one of two configurations (R or S) and both are within the scope of the present invention.

Alternatively, recombinant DNA technology may be employed wherein a nucleotide sequence which encodes a peptide of interest is inserted into an expression vector, transformed or transfected into an appropriate host cell and cultivated under conditions suitable for expression. These procedures are generally known in the art, as described generally in Sambrook et al.[29]

As the coding sequence for peptides of the length contemplated herein can be synthesized by chemical techniques, for example, the phosphotriester method of Matteucci, et al.[30], modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired recombinant protein.

The compounds described in this invention may be isolated as or converted to salts of various inorganic and organic acids and bases. Such salts are within the scope of this invention. Examples of such salts include ammonium, metal salts like sodium, potassium, calcium and magnesium; salts with organic bases like dicyclohexylamine, N-methyl-D-glucamine and the like; and salts with amino acids like arginine or lysine. Salts with inorganic and organic acids may be likewise prepared, for example, using hydrochloric, hydrobromic, sulfuric, phosphoric, trifluoroacetic, methanesulfonic, malic, maleic, fumaric and the like. Nontoxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a peptide of the invention with one or more molar equivalents of the desired acid or base in a solvent or solvent mixture in which the salt is insoluble; or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

The peptides employed in the subject invention need not be identical to peptides disclosed in the Example section, below, so long as the subject peptides are able to bind VLA-4 and inhibit intercellular adhesion. Thus, one of skill will recognize that a number of conservative substitutions can be made without substantially affecting the activity of the peptide. Conservative substitutions are those involving replacing an amino acid residue with another which is biologically and/or chemically similar, e.g., one hydrophobic residue for another, or one polar residue for another.

In particular, single amino acid substitutions, deletions, or insertions can be used to determine which residues are relatively insensitive to modification. Substitutions are preferably made with small, relatively neutral moieties such as Ala, Gly, Pro, or similar residues. The effect of single amino acid substitutions may also be probed using D-amino acids. The number and types of residues which are substituted or added depend on the spacing necessary between essential contact points and certain functional attributes which are sought (e.g., hydrophobicity versus hydrophilicity). Increased binding affinity for VLA-4 may also be achieved by such substitutions, compared to the affinity of the parent peptide. In any event, such substitutions should employ amino acid residues or other molecular fragments chosen to avoid, for example, steric and charge interference which might disrupt binding.

The substituting amino acids, however, need not be limited to those naturally occurring in proteins, such as L-α-amino acids, or their D-isomers. The peptides may be substituted with a variety of moieties such as amino acid mimetics well known to those of skill in the art.

In certain embodiments the peptides will include cysteine residues at both termini, which allow the production of cyclic peptides through disulfide linkages. For example, treatment of a such a peptide with an oxidizing agent such as oxygen, iodine or similar agent will produce a cyclic peptide which may be further purified using chromatographic or other methods of chemical purification. These cyclic peptides, which are conformationally restricted, provide probes for determining the spatial requirements at the adhesion signal binding site thereby providing information useful for the design of more potent peptides and non-peptidic molecules. Additionally, cyclic peptides, having the requisite binding affinity described above, are within the scope of this invention.

Construction of cyclic peptides can also be accomplished through thioether linkages. For instance, N-bromoacetyl-derivatized peptides can be reacted with sulfhydryl-containing residues, such as cysteine. Cyclization occurs by reaction of the free sulfhydryl of cysteine in the peptide with the bromoacetyl group to form a thioether linkage (Robey et.[31] and U.S. Pat. No. 5,066,716[32]).

Other methods of constructing cyclic peptides are known to those skilled in the art. These include side chain-side chain, side chain-main chain and main chain-main chain cyclizations. In addition, linkers can be used to join the amino and carboxyl termini of a peptide. The linker is capable of forming covalent bonds to both the amino and carboxyl terminus. Suitable linkers are well known to those of skill in the art and include, but are not limited to, straight or branched-chain carbon linkers, heterocyclic carbon linkers, or peptide linkers. The linkers may be joined to the carboxyl and amino terminal amino acids through their side groups (e.g., through a disulfide linkage to cysteine) or through the alpha carbon amino and carboxyl groups of the terminal amino acids.

In certain embodiments, the peptides will include a cysteine residue only at the C-terminus, which allow for the production of dimeric peptides through disulfide linkages. For example, treatment of such a peptide with an oxidizing agent such as oxygen, iodide or similar agent will produce a dimeric peptide which may be further purified using chromatographic or other methods of chemical purification.

The peptides of the invention can comprise modifications to the N- and/or C-terminal residues. As will be well understood by the artisan, the N- and C-termini may be modified to alter physical or chemical properties of the peptide, such as, for example, to affect binding, stability, bioavailability, ease of linking, and the like.

The N terminal residue can be modified to include acyl groups, in particular acetyl groups. Generally, the modifications will be of the formula $R_4$—CO— wherein, $R_4$ is lower alkyl, cycloalkyl, aryl, arylalkyl, or $R_5O$—. $R_5$ is lower alkyl, cycloalkyl, aryl or arylalkyl.

Preferred modifications of the C-terminus include modification of the carbonyl carbon of the C-terminal residue to form a carboxy-terminal amide or ester. In general, the amide nitrogen, covalently bound to the carbonyl carbon on the C-terminal residue, will have two substitution groups, each of which can be hydrogen, lower alkyl, aryl, cycloalkyl or alkylaryl group. Where the C-terminal residue is linked to an ester the group will generally have the formula —O—$R_6$ wherein, $R_6$ is lower alkyl, cycloalkyl, aryl and arylalkyl.

The N- or C-terminal residue may be linked to a variety of moieties other than amino acids such as polyethylene glycols to increase serum half life and provide other desired properties.

The biological activity of the peptides identified above may be assayed in a variety of systems. For example, a compound can be immobilized on a solid surface and adhesion of cells expressing VLA-4 can be measured. Using such formats, large numbers of specific modifications, (e.g., substitutions, deletions or additions) can be screened. Cells suitable for this assay include any leukocytes known to express VLA-4 such as T cells, B cells, monocytes, and eosinophils, basophils. A number of leukocyte cell lines can also be used, examples include Jurkat, and U937.

The test compounds can also be tested for the ability to competitively inhibit binding between VLA-4 and VCAM-1, or between VLA-4 and a labelled compound known to bind VLA-4, such as peptides of the invention or antibodies to VLA-4. In these assays the VCAM-1 can be immobilized on a solid surface. Alternatively, VCAM-1 expressing cells, such as activated endothelial cells or VCAM-1 transfected fibroblasts can be used. For assays to measure the ability to block adhesion to brain endothelial cells, the assays described in WO 91/05038[33] are particularly preferred.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3$H, $^{125}$I, $^{35}$S, $^{14}$C, or $^{32}$P labelled compounds or the like. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

Appropriate in vivo models for demonstrating efficacy in treating inflammatory responses include EAE in mice, rats or guinea pigs, as well as other inflammatory models dependent upon α4 integrins.

Peptides having the desired biological activity may be modified as necessary to provide desired properties such as improved pharmacological properties (e.g., in vivo stability, bio-availability), or the ability to be detected in diagnostic applications. For instance, inclusion of one or more D-amino acids in the peptide typically increases in vivo stability, particularly if the D-amino acid residues are substituted at one or both termini of the peptide sequence. Stability can be assayed in a variety of ways such as by measuring the half-life of the proteins during incubation with peptidases or human plasma or serum. A number of such protein stability assays have been described (see, e.g., Verhoef, et al.[34]).

For diagnostic purposes, a wide variety of labels may be linked to the peptides, which may provide, directly or indirectly, a detectable signal. Thus, the peptides of the subject invention may be modified in a variety of ways for a variety of end purposes while still retaining biological activity. In addition, various reactive sites may be introduced at the terminus for linking to particles, solid substrates, macromolecules, or the like.

Labeled peptides can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

In vitro uses include diagnostic applications such as monitoring inflammatory responses by detecting the presence of leukocytes expressing VLA-4. The peptides can also be used for isolating or labeling such cells. In addition, as mentioned above, the peptides of the invention can be used to assay for potential inhibitors of VLA-4/VCAM-1 interactions.

For in vivo diagnostic imaging to identify, e.g., sites of inflammation, radioisotopes are typically used in accordance with well known techniques. The radioisotopes may be bound to the peptide either directly or indirectly using intermediate functional groups. For instance, chelating agents such as diethylenetriaminepentacetic acid (DTPA) and ethylenediaminetetraacetic acid (EDTA) and similar molecules have been used to bind proteins to metallic ion radioisotopes.

The complexes can also be labeled with a paramagnetic isotope for purposes of in vivo diagnosis, as in magnetic resonance imaging (MRI) or electron spin resonance (ESR), both of which were well known. In general, any conventional method for visualizing diagnostic imaging can be used. Usually gamma- and positron-emitting radioisotopes are used for camera imaging and paramagnetic isotopes are used for MRI. Thus, the peptides can be used to monitor the course of amelioration of an inflammatory response in an individual. By measuring the increase or decrease in lymphocytes expressing VLA-4 it is possible to determine whether a particular therapeutic regimen aimed at ameliorating the disease is effective.

The pharmaceutical compositions of the present invention can be used to block or inhibit cellular adhesion associated with a number of diseases and disorders. For instance, a number of inflammatory disorders are associated with integrins or leukocytes. Treatable disorders include, e.g., allograft rejection, Alzheimer's disease, atherosclerosis, AIDS demential, diabetes, retinitis, cancer metastases, rheumatoid arthritis, acute leukocyte-mediated lung injury (e.g., adult respiratory distress syndrome), asthma, nephritis, and acute and chronic inflammation, including atopic dermatitis, psoriasis, myocardial ischemia, and inflammatory bowel disease. In preferred embodiments the pharmaceutical compositions are used to treat inflammatory brain disorders, such as multiple sclerosis (MS), viral meningitis and encephalitis.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer[35].

In order to enhance serum half-life, the peptides may be encapsulated, introduced into the lumen of liposomes, prepared as a colloid, or other conventional techniques may be employed which provide an extended serum half-life of the peptides. A variety of methods are available for preparing liposomes, as described in, e.g., Szoka, et al.[36], U.S. Pat. Nos. 4,235,871[37], 4,501,728[38] and 4,837,028[39].

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The pharmaceutical compositions are intended for parenteral, intranasal, sub-cutaneous, topical, oral or local administration, such as by aerosol or transdermally, for prophylactic and/or therapeutic treatment. Commonly, the pharmaceutical compositions are administered parenterally, e.g., intravenously. Thus, the invention provides compositions for parenteral administration which comprise peptide dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents (e.g., nonionic surfactants such as Tween, Pluronics) and the like, for example, sodium acetate, sodium lactate, sodium chloride, potassium chloride, calcium chloride, sorbitan monolaurate, and triethanolamine oleate. In addition the compositions may comprise antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the peptide preparations typically will be between 3 and 11, more preferably from 5 to 9 and most preferably from 7 and 8. It will be understood that use of certain of the foregoing excipients, carriers, or stabilizers will result in the formation of peptide salts.

The concentration of peptides in the pharmaceutical formulations can vary widely, i.e., from less than about 0.01%, usually at or at least about 5% to as much as 50 to 75% by weight and will be selected primarily by fluid volumes, viscosities, etc., in accordance with the particular mode of administration selected.

The therapeutic dosage of the peptides of the present invention will vary according to, for example, the particular use for which the treatment is made, the manner of administration of the peptides, the health and condition of the patient, and the judgment of the prescribing physician. For example, for intravenous administration, the dose will typically be in the range of about 20 $\mu$g to about 500 $\mu$g per kilogram body weight, preferably about 100 $\mu$g to about 300 $\mu$g per kilogram body weight. Suitable dosage ranges for intranasal administration are generally about 0.1 pg to 1 mg per kilogram body weight. Effective doses can be extrapolated from dose-response curves derived from in vitro or animal model test systems.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, preferably 25–75%.

For aerosol administration, the peptides are preferably supplied in finely divided form along with a conventional non-toxic surfactant and a suitable propellant. Typical percentages of peptides are 0.01%–20% by weight, preferably 1%–10%; and of surfactant from 0.1%–20% by weight, preferably 0.25%–5%.

Two or more peptides of the invention may be combined to form a peptide "cocktail" under certain circumstances for increased efficacy. The peptides of the invention may also be used in conjunction with other pharmaceutically active agents.

The following examples are offered to illustrate this invention and are not to be construed in any way as limiting the scope of this invention. Unless otherwise stated, all temperatures are in degrees Celsius. Also, in these examples, unless otherwise defined below, the abbreviations employed have their generally accepted meaning:

Å=Angstroms
BSA=bovine serum albumin
cm=centimeter
DCC=N,N-dicyclohexylcarbodiimide
DMF=dimethylformamide
E-64=trans-epoxysuccinyl-L-leucylamido-(4-guanidino) butane
FACS=fluorescent activated cell sorter
FMOC=fluorenylmethoxycarbonyl
HBTU=O-benzotriazol-1-yl-N,N,N',N'-tetramethyluronium hexaflurophosphate
HOBT=1-hydroxybenzotriazole
HPLC=high performance liquid chromatography
I.D.=internal diameter
MBHA=methyl benzhydrylamine
mg=milligram
mL=milliliter
mmole=millimole
mM=millimolar
N=normal
PAM=phenylacetamidomethyl
PMSF=phenylmethylsulfonyl fluoride ($\alpha$-toluenesulfonyl fluoride)
TBTU=2-(1H-benzotriazol- 1-yl)- 1,1,3,3-tetramethyluronium
t-BOC=t-butyloxycarbonyl
TFA=trifluoroacetic acid
$\mu$g=micrograms
$\mu$L=microliters
$\mu$m=micron

EXAMPLE 1

Peptide Synthesis Using Fluorenylmethoxycarbonyl (FMOC) Protected Amino Acids

Peptides were synthesized on an automated Symphony Multiplex Peptide Synthesizer from Protein Technologies using instrument resident software. The syntheses were carried out on a 0.1 mmole scale utilizing FMOC protected amino acids. 4-Hydroxymethylphenoxymethyl polystyrene resin was used to obtain C-terminal carboxylic acid peptides and 4-(2',4'-dimethoxyphenyl-FMOC-aminomethyl) phenoxymethyl-polystyrene resin was used to produce C-terminal peptide amides. Amino acid side chains were protected as follows: Arg(2,2,5,7,8-pentamethylchroman-6-sulfonyl), Asp(t-butoxy), Glu(t-butoxy), Ser(t-butyl), Thr(t-butyl), Tyr(t-butyl), Asn(trityl), Gln(trityl), His(trityl), Lys (t-butoxycarbonyl), Cys (S-trityl).

FMOC amino acids were dissolved in DMF to 200 mM concentrations. Each FMOC amino acid was activated, in situ, to its corresponding active ester using 200 mM HBTU/ 0.4 mM N-methyl-morpholine in DMF. Following removal of the FMOC protecting group from the previous amino acid addition using 20% piperidine in DMF, a five fold excess of the FMOC amino acid was added followed by an equimolar amount of activator. The amino acid active ester was formed in situ and allowed to react for twenty minutes. The peptide resin was then washed in DMF and dichloromethane and any uncoupled amine was capped using 10% acetic anhydride in dichloromethane. At this point the synthesis cycle was repeated beginning with FMOC deprotection.

After the synthesis cycles were complete, the final FMOC group was removed with 20% piperidine in DMF and at this point the N-terminal was N-acetylated if so desired. Each peptide resin was then cleaved from the resin support and stripped of any remaining side chain protecting groups by treatment for 2 hours with 50% TFA in dichloromethane. Crude peptides were precipitated by the addition of cold diethyl ether. The precipitate was centrifuged, the solvent removed, and the precipitate washed with cold diethyl ether and centrifuged two more times. The crude peptide precipitate was then dissolved in aqueous 2N acetic acid and lyophilized. The peptides produced using this automated FMOC protocol were purified as described in Example 2 for those peptides produced using t-BOC chemistry.

EXAMPLE 2

Peptide Synthesis Using t-BOC Protection

Peptides were synthesized on an Applied Biosystems Model 430A Peptide Synthesizer using modified double couple capping cycles for each amino acid addition. The syntheses were carried out on a 0.5 mmole scale. Peptides which are C-terminal carboxylic acids were synthesized on PAM polystyrene resins which give the desired peptide acid following HF treatment. C-terminal peptide amides were synthesized on MBHA polystyrene resin. Amino acid side chain protection was as follows: Arg(p-toluenesulfonyl), Asp(benzyl), Glu(benzyl), Cys(4-methylbenzyl), His(t-butyloxymetyl), Lys(4-chlorobenzyloxycarbonyl), Ser (benzyloxy), Thr(benzyloxy), Tyr(4-bromobenzyloxycarbonyl). All other amino acids were used with no further side chain protection.

Amino acids were coupled following preactivation to the symmetric anhydride using 0.5 equivalent of DCC in dichloromethane. Glutamine and asparagine were preactivated to their respective HOBT esters using 1 equivalent of DCC and 1 equivalent of HOBT in dimethylformamide. Capping of any uncoupled amine with 10% acetic anhydride in dichloromethane followed the recoupling step for each amino acid addition. The capping protocol was used to minimize synthesis of deletion peptides which are often difficult to separate from the target peptide. The BOC protecting group on each amino acid α-amine was removed with 50% trifluoroacetic acid in dichloromethane. Following removal of the BOC group on the final amino acid and N-terminal acetylation if desired, the peptides were cleaved from the resin support with anhydrous hydrogen fluoride which concurrently removes any remaining side chain protecting groups. The HF cleavage and deprotection was accomplished in 1 hour at 0° C. in the presence of anisole as a scavenger and with the addition of methylethylsulfide for peptides containing methionine or cysteine. Following HF treatment, the peptide was extracted from the resin in 2N acetic acid and lyophilized.

The crude peptide was then purified using preparative reverse phase HPLC on Vydac C4 or C18, 330 Å, 10 μm columns that are 2.2 cm I.D.×25 cm in length. The system of choice was 0.1% TFA/H$_2$O (A buffer) and 0.1% TFA/ CH$_3$CN (B buffer) as the mobile phase. Typically the peptide was loaded onto the column in 2% B buffer at 8–10 mL/minute and eluted using a linear gradient of 2% B buffer to 60% B buffer in 174 minutes.

The purified peptide was characterized by amino acid analysis, mass spectrometry, and analytical reverse phase HPLC and, if required, sequence analysis.

EXAMPLE 3

Disulfide Bonded Cyclic and Dimeric Peptides

Peptides synthesized in Examples 1 and 2 which contain cysteine residues were cyclized or dimerized via the formation of either an intramolecular (cyclic form) or intermolecular (dimeric form) disulfide bond. The crude peptide, following cleavage from the resin and lyophilization from 2N acetic acid, was made to a concentration of 1 mg/mL in glacial acetic acid. A ten-fold molar excess of iodine, dissolved in the minimum amount of glacial acetic acid, was added dropwise to the peptide solution over a period of ca. 60 minutes. Upon completion of the addition, the reaction was continued for 4 hours at room temperature. The reaction solution was then treated with zinc dust to consume unreacted iodine, filtered and concentrated. The residual product was lyophilized from 2N acetic acid. The crude product was then purified as described in Example 2.

The peptides were also cyclized or dimerized by air oxidation to form disulfide bonds. In this case, the peptide was dissolved at ≈0.5 mg/mL in NH$_4$OAc pH 8.5 and stirred gently in a flask open to the air. The reaction progress was monitored by HPLC and Ellman analysis to detect free sulfhydryl groups.

Dimerization occurs when the peptide contains a single cysteine residue whereas cyclization, as per above, can occur when the peptide contains two or more cysteine residues.

EXAMPLE 4

Thioether Cyclization

Peptides having a C-terminal Cys residue and an N-terminal Br-Acetyl- can be cyclized via formation of an intramolecular thioether (see, Robey et al.[31]).

To form the thioether, the pH of the peptide in 200–500 mL aqueous acetic acid was adjusted to 8.5 by slowly adding NH$_4$OH (ammonium hydroxide). When the pH was stabilized, the solution was stirred for at least 4 hours at room temperature. When thioether formation was complete, the solution was loaded directly onto a preparative HPLC column for desalting or lyophilized.

EXAMPLE 5

Adhesion of Jurkat Cells to Peptide-BSA Conjugates

This example demonstrates that a peptide derived from the antibody 21/6 CDR3 region interacts specifically with VLA-4 integrin.

The peptide used in this example was synthesized based on the sequence of the anti-α$_4$ integrin antibody 21/6 (CGGEGYYGNYGVYA, SEQ ID No. 1). In this example the peptide was conjugated to a large carrier protein via the linker region that was synthesized as part of the peptide itself (in italics). The conjugated peptide was then coated onto plastic, and the ability of the conjugate to support cell adhesion was tested. This method is based on a report by Wayner and Kovach[40].

As a positive control, the fibronectin peptide described by Wayner was synthesized, conjugated to carrier protein, and tested for cell adhesion in parallel with SEQ ID NO. 1 (CGGEILDVPST, SEQ ID No. 2). Both peptide conjugates were exposed to the plastic at a concentration of 3 μg/mL. As shown in FIG. 1, Jurkat cells bound equally well to the two peptides, but did not bind control protein. Adhesion was not affected by an antibody against $\beta_2$ integrin (IOT18), a distinct cell adhesion molecule that is also expressed on the surface of Jurkat cells. Thus, like peptide SEQ ID NO. 2, peptide SEQ ID NO. 1 interacts with Jurkat in an $\alpha_4$ integrin-specific fashion.

EXAMPLE 6

Jurkat Interaction with Soluble VCAM-1

This example demonstrates that peptides derived from the antibody 21/6 CDR3 region can be used as competitive inhibitors of VLA-4 integrin interaction with VCAM-1.

VCAM-1 was expressed as a soluble fusion protein. The construct expressed the seven extracellular domains of VCAM-1 on the N-terminus, and the human $IgG_1$ heavy chain constant region on the C-terminus. Interaction of the soluble construct with Jurkat cells was monitored by standard FACS analysis, using a fluorescently labeled antibody directed against the construct's human IgG tail as a marker.

The activity of VLA-4 can be regulated. 15/7 is a monoclonal antibody that recognizes an activated conformation of VLA-4 and locks the molecule in the active state, thereby enhancing VLA-4-mediated cell adhesion. 15/7 stabilizes the interaction of Jurkat cells with the soluble VCAM-1 construct.

When mixed with Jurkat cells in the presence of $Mn^{+2}$ and 15/7, the soluble VCAM-1 construct interacted with the cell surface in an VLA-4-dependent fashion; the interaction was inhibited completely by anti-α4 integrin (21/6), but not by the IOT18 antibody against $\beta_2$ integrin (data not presented).

FIG. 2 shows that peptide SEQ ID No. 4, derived from the CDR3 region of the anti-α4 integrin antibody 21/6 (EGYYGNYGVYA)(SEQ ID NO: 4), inhibited interaction of sVCAM-1-IgG with Jurkat cells in a dose-dependent fashion. Truncation of the first two amino acids from the peptide's N-terminus had no significant effect on activity (SEQ ID No. 27), whereas truncation of the last alanine greatly increased inhibitory activity (SEQ ID No. 17).

EXAMPLE 7

Peptides from the Sequence of Antibody 21/6

This example summarizes data from several studies that examined the effect of specific peptide modifications on the activity of peptides derived from the antibody 21/6.

Peptides of different length, and with various amino acid substitutions were synthesized based on the sequence of the CDR3 region of the antibody 21/6 (EGYYGNYGVYA) (SEQ ID No. 4). The peptides were then tested for their ability to inhibit Jurkat interaction with sVCAM-1-IgG in the FACS assay described in Example 6. $IC_{50}$ values were determined for each peptide using this assay.

The sequence of peptides tested is provided in Table 1. N-acetylation is indicated by "[Ac]". This table also includes the expected and observed mass of each peptide used in the assays.

In one series of experiments, various amino acids were substituted with alanine (A) to determine the importance of the native amino sequence on the peptide's activity. These experiments demonstrated that both N-terminal tyrosines were crucial for activity, but that the other two tyrosines were not. In fact, substitution of the C-terminal tyrosine greatly enhanced the peptide's activity. In another series of experiments, amino acids were deleted from the N and C-terminus to determine the minimal length of the peptide required for activity. These results demonstrated that removal of the C-terminal alanine greatly increased the peptide's activity, but that activity was diminished by further deletions. These experiments define an eight amino acid domain (YYGNYGVY; SEQ ID NO: 163) (amino acids 3–10 of SEQ ID NO: 4) that is important for activity, and two crucial amino acids within this domain (the N-terminal YY). A short cyclic peptide with homology to this peptide (CYFQNC; pressinoic acid, SEQ ID No. 29) was also tested.

TABLE 1

Alanine Substitution Analysis

| Sequence ID | F.W. | Mass Found | Sequence | Form |
| --- | --- | --- | --- | --- |
| SEQ ID No. 3 | 915 | 915 | [Ac]EILDVPST | Linear |
| SEQ ID No. 4 | 1297 | 1298 | [Ac]EGYYGNYGVYA | Linear |
| SEQ ID No. 5 | 1255 | 1256 | EGYYGNYGVYA | Linear |
| SEQ ID No. 6 | 1239 | 1240 | [Ac]AGYYGNYGVYA | Linear |
| SEQ ID No. 7 | 1205 | 1206 | [Ac]EGAYGNYGVYA | Linear |
| SEQ ID No. 8 | 1205 | 1206 | [Ac]EGYAGNYGVYA | Linear |
| SEQ ID No. 9 | 1254 | 1249 | [Ac]EGYYGAYGVYA | Linear |
| SEQ ID No. 10 | 1311 | 1312 | [Ac]EGYYGQYGVYA | Linear |
| SEQ ID No. 11 | 1205 | 1205 | [Ac]EGYYGNAGVYA | Linear |
| SEQ ID No. 12 | 1205 | 1205 | [Ac]EGYYGNYGVAA | Linear |
| SEQ ID No. 13 | 1113 | 1113 | [Ac]EGAYGNAGVYA | Linear |
| SEQ ID No. 14 | 1113 | 1113 | [Ac]EGAYGNYGVAA | Linear |
| SEQ ID No. 15 | 1113 | 1113 | [Ac]EGYYGNAGVAA | Linear |
| SEQ ID No. 16 | 1021 | 1022 | [Ac]EGAYGNAGVAA | Linear |
| SEQ ID No. 17 | 1184 | 1185 | EGYYGNYGVY | Linear |
| SEQ ID No. 18 | 1021 | 1021 | EGYYGNYGV | Linear |
| SEQ ID No. 19 | 922 | 922 | EGYYGNYG | Linear |
| SEQ ID No. 20 | 865 | 865 | EGYYGNY | Linear |
| SEQ ID No. 21 | 702 | 702 | EGYYGN | Linear |
| SEQ ID No. 22 | 1226 | 1227 | [Ac]EGYYGNYGVY | Linear |
| SEQ ID No. 23 | 1063 | 1063 | [Ac]EGYYGNYGV | Linear |
| SEQ ID No. 24 | 964 | 964 | [Ac]EGYYGNYG | Linear |
| SEQ ID No. 25 | 907 | 908 | [Ac]EGYYGNY | Linear |
| SEQ ID No. 26 | 743 | 744 | [Ac]EGYYGN | Linear |
| SEQ ID No. 27 | 1111 | 1111 | [Ac]YYGNYGVYA | Linear |
| SEQ ID No. 28 | 1070 | 1070 | YYGNYGVYA | Linear |
| SEQ ID No. 29 | 775 | 775 | CYFQNC | Cyclic |

EXAMPLE 8

Peptides Derived from VCAM-1 Inhibit Jurkat Interaction with Soluble VCAM-1

This example demonstrates that specific peptides derived from the first domain of VCAM-1 can be used as competitive inhibitors of VLA-4 interaction with VCAM-1.

Peptides derived from the FGN region of VCAM-1 described above were tested as competitive inhibitors of Jurkat cell interaction with VCAM-1 (as described in example 6). The results are shown in Table 2, below. As in Table 1, N-acetylation is indicated by [Ac]. C-terminal amidation is indicated by [$NH_2$]. One peptide (SEQ ID No. 31) showed particularly good inhibition. Peptides from other regions of VCAM-1 were also tested, two of which were found to be inhibitory (SEQ ID No. 34 and SEQ ID No. 40). SEQ ID No. 34 contains the QID tripeptide which has previously been identified[41] as important for the interaction of VCAM-1 with VLA-4 integrin. A cyclic peptide derived from this sequence was more active than the linear peptide (SEQ ID No. 35). SEQ ID No. 40 is from a region of VCAM-1 adjacent to the FGN motif described above (the C-terminus of this peptide carries the F from FGN). This peptide has not been previously described and is quite active in a linear form. Two preferred peptides are cyclic peptides, SEQ ID Nos. 53 and 59.

TABLE 2

| Sequence ID | F.W. | Mass Found | Sequence | Form |
| --- | --- | --- | --- | --- |
| SEQ ID No. 30 | 1292 | 1292 | [Ac]PVSFGNEHSYL | Linear |
| SEQ ID No. 31 | 1115 | 1115 | CGFGNEHSYC | Cyclic |
| SEQ ID No. 32 | 896 | 894 | CFGNEHSC | Cyclic |
| SEQ ID No. 33 | 1285 | 1284 | ESPFFSWRTQ | Linear |
| SEQ ID No. 34 | 1202 | 1202 | SWRTQIDSPL | Linear |
| SEQ ID No. 35 | 923 | 923 | CRTQIDSC | Cyclic |
| SEQ ID No. 36 | 1039 | 1037 | CGRTQIDSGC | Cyclic |
| SEQ ID No. 37 | 1044 | 1043 | IDSPLNGKVT | Linear |
| SEQ ID No. 38 | 1021 | 1019 | NGKVTNEGTT | Linear |
| SEQ ID No. 39 | 1055 | 1055 | NEGTTSTLTM | Linear |
| SEQ ID No. 40 | 1097 | 1096 | STLTMNPVSF | Linear |
| SEQ ID No. 41 | 1177 | 1177 | [Ac]EGYYGNYGAAA | Linear |
| SEQ ID No. 42 | 1270 | 1270 | [Ac]EGYYGNYGAYA | Linear |
| SEQ ID No. 43 | 1255 | 1255 | [Ac]EGYYGNYGGYA | Linear |
| SEQ ID No. 44 | 1311 | 1312 | [Ac]EGYYGNYAVYA | Linear |
| SEQ ID No. 45 | 1111 | 1111 | [Ac]YYGNYGVYA | Linear |
| SEQ ID No. 46 | 704 | 704 | CYFGNC | Cyclic |
| SEQ ID No. 47 | 746 | 746 | [Ac]CYFGNC | Cyclic |
| SEQ ID No. 48 | 824 | 824 | CYFGQC | Cyclic |
| SEQ ID No. 49 | 753 | 753 | CYFGYC | Cyclic |
| SEQ ID No. 50 | 769 | 769 | CYYGYC | Cyclic |
| SEQ ID No. 51 | 734 | 734 | CYYGQC | Cyclic |
| SEQ ID No. 52 | 672 | 675 | [Ac]YYGQC | Cyclic |
| SEQ ID No. 53 | 677 | 677 | CYYGAC | Cyclic |
| SEQ ID No. 54 | 616 | 616 | [Ac]YYGAC | Cyclic |
| SEQ ID No. 55 | 628 | 628 | CAYGNC | Cyclic |
| SEQ ID No. 56 | 566 | 566 | [Ac]AYGNC | Cyclic |
| SEQ ID No. 57 | 628 | 628 | CYAGNC | Cyclic |
| SEQ ID No. 58 | 567 | 567 | [Ac]YAGNC | Cyclic |
| SEQ ID No. 59 | 792 | 792 | CYYENC | Cyclic |
| SEQ ID No. 60 | 731 | 731 | [Ac]YYENC | Cyclic |
| SEQ ID No. 61 | 883 | 883 | CYYGYNC | Cyclic |
| SEQ ID No. 62 | 822 | 822 | [Ac]YYGYNC | Cyclic |
| SEQ ID No. 63 | 1220 | 1220 | CYFGNEHSYCG | Cyclic |
| SEQ ID No. 64 | 906 | 906 | EGYYGNY[NH$_2$] | Linear |
| SEQ ID No. 65 | 1062 | 1062 | [Ac]EGYYGNYGV[NH$_2$] | Linear |

EXAMPLE 9

Peptide Derivatives

Other peptides, derived from those of Tables 1 and 2 above, were prepared and are set forth in Table 3 below:

TABLE 3

| Sequence ID | F.W. | Mass Found | Sequence | Form |
| --- | --- | --- | --- | --- |
| SEQ ID No. 66 | 1073 | 1073 | NPVSFGNEHS | Linear |
| SEQ ID No. 67 | 837 | 836 | [Ac]TMNPVSF | Linear |
| SEQ ID No. 68 | 1346 | 1345 | AyFGNC AyFGNC | Dimer |
| SEQ ID No. 69 | 1363 | 1363 | [Ac]PVSFENEHSYL | Linear |
| SEQ ID No. 70 | 950 | 950 | [Ac]LTMNPVSF | Linear |
| SEQ ID No. 71 | 1312 | 1311 | AYFGPC AYFGPC | Dimer |
| SEQ ID No. 72 | 662 | 662 | [Ac]NPVSFG | Linear |
| SEQ ID No. 73 | 748 | 748 | CyYEAC[NH$_2$] | Cyclic |
| SEQ ID No. 74 | 716 | 716 | [Ac]GYYGNC | Cyclic |
| SEQ ID No. 75 | 605 | 605 | [Ac]NPVSF | Linear |
| SEQ ID No. 76 | 659 | 659 | [Ac]YYGNC | Cyclic |
| SEQ ID No. 77 | 1110 | 1110 | [Ac]YYGNYGVYA[NH$_2$] | Linear |
| SEQ ID No. 78 | 645 | 645 | [Ac]FGNEH | Linear |

TABLE 3-continued

| Sequence ID | F.W. | Mass Found | Sequence | Form |
| --- | --- | --- | --- | --- |
| SEQ ID No. 79 | 1051 | 1050 | [Ac]TLTMNPVSF | Linear |
| SEQ ID No. 80 | 643 | 643 | [Ac]yFGNC | Cyclic |
| SEQ ID No. 81 | 840 | 840 | CYYQYC | Cyclic |
| SEQ ID No. 82 | 491 | 491 | [Ac]PVSF | Linear |
| SEQ ID No. 83 | 736 | 736 | [Ac]MNPVSF | Linear |
| SEQ ID No. 84 | 704 | 704 | CyFGNC | Cyclic |
| SEQ ID No. 85 | 595 | 595 | [Ac]dFGNC | Cyclic |
| SEQ ID No. 86 | 822 | 822 | [Ac]YYGNYC | Cyclic |
| SEQ ID No. 87 | 1138 | 1137 | [Ac]STLTMNPVSF | Linear |
| SEQ ID No. 88 | 656 | 656 | CdFGNC | Cyclic |
| SEQ ID No. 89 | 687 | 687 | CYFGPC | Cyclic |
| SEQ ID No. 90 | 636 | 635 | [Ac]rFGNC | Cyclic |
| SEQ ID No. 91 | 697 | 697 | CrFGNC | Cyclic |
| SEQ ID No. 92 | 611 | 611 | [Ac]mFGNC | Cyclic |
| SEQ ID No. 93 | 672 | 672 | CmFGNC | Cyclic |
| SEQ ID No. 94 | 593 | 592 | [Ac]lFGNC | Cyclic |
| SEQ ID No. 95 | 654 | 654 | ClFGNC | Cyclic |
| SEQ ID No. 96 | 579 | 579 | [Ac]vFGNC | Cyclic |
| SEQ ID No. 97 | 640 | 640 | CvFGNC | Cyclic |
| SEQ ID No. 98 | 567 | 567 | [Ac]sFGNC | Cyclic |
| SEQ ID No. 99 | 628 | 628 | CsFGNC | Cyclic |
| SEQ ID No. 100 | 595 | 595 | [Ac]DFGNC | Cyclic |
| SEQ ID No. 101 | 636 | 636 | [Ac]RFGNC | Cyclic |
| SEQ ID No. 102 | 611 | 611 | [Ac]MFGNC | Cyclic |
| SEQ ID No. 103 | 593 | 593 | [Ac]LFGNC | Cyclic |
| SEQ ID No. 104 | 579 | 579 | [Ac]VFGNC | Cyclic |
| SEQ ID No. 105 | 567 | 567 | [Ac]SFGNC | Cyclic |
| SEQ ID No. 106 | 627 | 627 | [Ac]fFGNC | Cyclic |
| SEQ ID No. 107 | 688 | 688 | CfFGNC | Cyclic |
| SEQ ID No. 108 | 656 | 656 | CDFGNC | Cyclic |
| SEQ ID No. 109 | 697 | 696 | CRFGNC | Cyclic |
| SEQ ID No. 110 | 672 | 672 | CMFGNC | Cyclic |
| SEQ ID No. 111 | 1264 | 1264 | AiLDVC AiLDVC | Dimer |
| SEQ ID No. 112 | 633 | 633 | AiLDVC | Linear |
| SEQ ID No. 113 | 1264 | 1264 | AiLDVC AiLDVC | Dimer |
| SEQ ID No. 114 | 658 | 658 | AfGNC | Linear |
| SEQ ID No. 115 | 1313 | 1313 | AfGNC AfGNC | Dimer |
| SEQ ID No. 116 | 633 | 633 | AlLDVC | Linear |
| SEQ ID No. 117 | 716 | 715 | CsFEDC[NH$_2$] | Cyclic |
| SEQ ID No. 118 | 717 | 717 | CsFEDC | Cyclic |
| SEQ ID No. 119 | 717 | 717 | CSFEDC | Cyclic |
| SEQ ID No. 120 | 654 | 654 | CLFGNC | Cyclic |
| SEQ ID No. 121 | 640 | 639 | CVFGNC | Cyclic |
| SEQ ID No. 122 | 749 | 749 | CyYEAC | Cyclic |
| SEQ ID No. 123 | 1522 | 1522 | AYYENC AYYENC | Dimer |
| SEQ ID No. 124 | 778 | 778 | SYYENC | Linear |
| SEQ ID No. 125 | 1554 | 1554 | SYYENC SYYENC | Dimer |
| SEQ ID No. 126 | 628 | 627 | CSFGNC | Cyclic |
| SEQ ID No. 127 | 749 | 749 | CYYEAC | Cyclic |
| SEQ ID No. 128 | 677 | 677 | CyYGAC | Cyclic |
| SEQ ID No. 129 | 791 | 791 | CYYENC[NH$_2$] | Cyclic |
| SEQ ID No. 130 | 735 | 735 | CYYdAC | Cyclic |
| SEQ ID No. 131 | 674 | 674 | AyFGNC | Linear |
| SEQ ID No. 132 | 1345 | 1345 | AYFGNC AYFGNC | Dimer |
| SEQ ID No. 133 | 719 | 719 | AyYEAC | Linear |
| SEQ ID No. 134 | 676 | 676 | CYYGAC[NH$_2$] | Cyclic |
| SEQ ID No. 135 | 663 | 663 | CYYGGC | Cyclic |
| SEQ ID No. 136 | 735 | 735 | CYYDAC | Cyclic |
| SEQ ID No. 137 | 691 | 691 | CYYAAC | Cyclic |
| SEQ ID No. 138 | 792 | 792 | CyYENC | Cyclic |
| SEQ ID No. 139 | 749 | 749 | CYYeAC | Cyclic |
| SEQ ID No. 140 | 1436 | 1435 | AyYEAC AyYEAC | Dimer |
| SEQ ID No. 141 | 762 | 762 | AyYENC | Linear |
| SEQ ID No. 142 | 657 | 657 | AYFGPC | Linear |
| SEQ ID No. 143 | 1249 | 1250 | ADFGNC ADFGNC | Dimer |
| SEQ ID No. 144 | 1704 | 1704 | AYYGYNC AYYGYNC | Dimer |
| SEQ ID No. 145 | 626 | 626 | [Ac]YFGPC | Cyclic |
| SEQ ID No. 146 | 721 | 721 | CYYGdC | Cyclic |
| SEQ ID No. 147 | 735 | 735 | CYYGEC | Cyclic |
| SEQ ID No. 148 | 721 | 721 | CYYGDC | Cyclic |
| SEQ ID No. 149 | 735 | 735 | CYYGeC | Cyclic |
| SEQ ID No. 150 | 1292 | 1292 | AyYGAC AyYGAC | Dimer |
| SEQ ID No. 151 | 853 | 853 | AYYGYNC | Linear |
| SEQ ID No. 152 | 674 | 674 | AYFGNC | Linear |
| SEQ ID No. 153 | 647 | 647 | AyYGAC | Linear |
| SEQ ID No. 154 | 1522 | 1521 | AyYENC AyYENC | Dimer |

TABLE 3-continued

| Sequence ID | F.W. | Mass Found | Sequence | Form |
|---|---|---|---|---|
| SEQ ID No. 155 | 626 | 626 | ADFGNC | Linear |
| SEQ ID No. 156 | 676 | 676 | CyYGAC[NH$_2$] | Cyclic |
| SEQ ID No. 157 | 791 | 791 | CyYENC[NH$_2$] | Cyclic |

In the tables above, peptides recited as "cyclic" having a [Ac] group at the N-terminus are cyclic thioethers of the general formula:

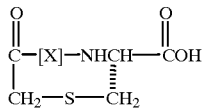

where [X] represents the residues between the N-terminal [Ac] and the C-terminal cysteine residues.

Of the peptides set forth in Tables 1, 2 and 3 above, peptides defined by SEQ ID Nos. 4, 9, 12, 15, 17, 22, 31, 32, 35, 40, 41, 42, 43, 45, 52, 54, 60, 62, 63, 71, 94, 96, 123, 124, 125, 133, 140, 142, 144, 150, 154 each bound to VLA-1 and had an IC$_{50}$ (per Example 6 above) of 50 $\mu$M or less.

EXAMPLE 10

Cell Free Assay to Measure the Interaction of $\alpha_4\beta_1$ Integrin With VCAM-1

In this assay, Jurkat cells are lysed with a detergent to solubilize $\alpha_4\beta_1$ integrin [15×10$^6$ Jurkat cell/mL, 1% n-octyl $\beta$-D-glucopyranoside (Sigma #0-8001) with 150 mM NaCl, 1 mM CaCl$_2$, 1 mM MgCl$_2$, 1 mM MnCl$_2$, pH 7.4, and the protease inhibitors PMSF, E-64, and leupeptin]. An antibody against $\beta_1$ integrin, TS2/16 (ATCC #HB-243, from the American Type Tissue Collection, Rockville, Md., USA) is added to the lysate. TS 2/16 is an activating antibody against $\beta$1 integrin that promotes $\beta_1$ integrin-dependent interactions[42,43], thereby increasing the activity of solubilized $\alpha_4\beta_1$ integrin in the assay. The ascites was diluted 1:1000–1:3000 in the assay.

200 $\mu$L of the lysate (with TS2/16) is added to microtiter wells (on a 96 well plate) and 20 $\mu$L of 10× test compound is added to the lysate for 30 minutes at 4° C. 50 $\mu$L of the treated lysate is added to triplacate wells of a 96 well plate coated with sVCAM-1-IgG (wells of a 96 well plate are coated with sVCAM-1-IgG, 10 $\mu$g/mL, 50 $\mu$L/well, overnight at 4° C. and the wells then blocked with 1% BSA), and then adhesive incubation is allowed to occur for 30 minutes at room temperature. The plate is then washed, blocked with 1% BSA, and the exposed to alkaline phosphatase-conjugated goat anti-mouse Ig (BioRad #170-6520), which recognizes TS2/16 associated with $\alpha_4\beta_1$ integrin that has bound sVCAM-1-IgG on the assay well. After 30 minutes at room temperature, the wells are washed and exposed to a substrate for alkaline phosphatase (2-amino-2-methyl-1-propanol) to quantify the amount of $\alpha_4\beta_1$ integrin that has bound the sVCAM-1-IgG.

The results of the IC$_{50}$ values for several peptides described herein are comparable with the IC$_{50}$ values obtained via the assay of Example 6 above.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A VLA-4 binding peptide, comprising a peptide having 10 or fewer amino acids which includes the sequence YYGN (SEQ ID NO: 158), wherein said peptide has a binding affinity to VLA-4, as evidenced by an $IC_{50}$ of less than about 50 μM for inhibiting binding between VLA-4 and VCAM-1.

2. A pharmaceutical composition comprising a pharmaceutically acceptable carrier and a therapeutically effective amount of a peptide of claim 1.

3. The pharmaceutical composition of claim 2, wherein the peptide is selected from the group consisting of: SEQ ID NOs. 4, 9, 12, 15, 17, 22, 31, 32, 40, 41, 42, 43, 45, 52, 54, 60, 62, 63, 71, 94, 96, 123, 124, 125, 133, 140, 142, 144, 150, and 154.

4. A method of treating an inflammatory disease, comprising administering to a patient exhibiting inflammation a pharmaceutical composition comprising a pharmaceutically acceptable carrier and a therapeutically effective amount of a peptide of claim 1.

5. The method of claim 4, wherein the inflammatory disease is an inflammatory brain disorder.

6. The method of claim 5, wherein the inflammatory brain disorder is multiple sclerosis.

7. A method of inhibiting the adhesion of leukocytes mediated by VLA-4 which method comprises contacting the cells with a composition comprising a peptide of claim 1.

8. The peptide of claim 1, wherein said binding affinity to VLA-4 is evidenced by an $IC_{50}$ that is less than an $IC_{50}$ exhibited by a peptide selected from the group consisting of SEQ ID NO: 4, SEQ ID NO: 9, SEQ ID NO: 12, SEQ ID NO: 15, SEQ ID NO: 17, SEQ ID NO: 22, SEQ ID NO: 31, SEQ ID NO: 32, SEQ ID NO: 40, SEQ ID NO: 41, SEQ ID NO: 42, SEQ ID NO: 43, SEQ ID NO: 45, SEQ ID NO: 52, SEQ ID NO: 54, SEQ ID NO: 60, SEQ ID NO: 62, SEQ ID NO: 63, SEQ ID NO: 71, SEQ ID NO: 94, SEQ ID NO: 96, SEQ ID NO: 123, SEQ ID NO: 124, SEQ ID NO: 125, SEQ ID NO: 133, SEQ ID NO: 140, SEQ ID NO: 142, SEQ ID NO: 144, SEQ ID NO: 150, and SEQ ID NO: 154.

9. The peptide of claim 1, wherein said peptide is between 6 and 10 amino acids in length.

10. The peptide of claim 1, which includes the sequence YYGNYGVY.

11. The peptide of claim 1, wherein one or more of the amino acid residues in said peptide is optionally a D-amino acid residue, further wherein the N-terminus of said peptide is optionally modified by linkage to the amine group of a group having the formula $R_4$—CO—, wherein $R_4$ is selected from the group consisting of hydrogen, lower alkyl, cycloalkyl, aryl, and arylalkyl, or by linkage to the amine group of a group having the formula $R_5O$—, wherein $R_5$ is selected from the group consisting of lower alkyl, cycloalkyl, aryl and arylalkyl; and still further wherein the C-terminus of said peptide is optionally modified by linkage of the carbonyl to a group selected from O—$R_6$ and

wherein $R_6$ is selected from the group consisting of lower alkyl, cycloalkyl, aryl and aryl alkyl, and $R_7$ and $R_8$ are the same or different and are selected from the group consisting of hydrogen, lower alkyl, cycloalkyl, aryl and arylalkyl.

12. A VLA-4 binding peptide, comprising a peptide consisting of 13 or fewer amino acids which includes the sequence SEQ ID NO: 163, wherein said peptide has a binding affinity to VLA-4, as evidenced by an $IC_{50}$ of less than about 50 μM for inhibiting binding between VLA-4 and VCAM-1.

13. The peptide of claim 2, wherein said peptide is selected from the group consisting of SEQ ID NO: 4, SEQ ID NO: 17, SEQ ID NO: 22, and SEQ ID NO: 45.

* * * * *